(12) United States Patent
Abolmaesumi et al.

(10) Patent No.: US 10,751,029 B2
(45) Date of Patent: Aug. 25, 2020

(54) ULTRASONIC IMAGE ANALYSIS

(71) Applicant: The University of British Columbia, Vancouver (CA)

(72) Inventors: Purang Abolmaesumi, Vancouver (CA); Robert Rohling, Vancouver (CA); Teresa Tsang, North Vancouver (CA); Zhibin Liao, Adelaide (AU); Amir Abdi, Vancouver (CA)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 16/557,261

(22) Filed: Aug. 30, 2019

(65) Prior Publication Data
US 2020/0069292 A1 Mar. 5, 2020

Related U.S. Application Data

(63) Continuation of application No. PCT/CA2019/051192, filed on Aug. 28, 2019.
(Continued)

(51) Int. Cl.
*A61B 8/08* (2006.01)
*A61B 8/00* (2006.01)

(52) U.S. Cl.
CPC .......... *A61B 8/5207* (2013.01); *A61B 8/0883* (2013.01); *A61B 8/463* (2013.01);
(Continued)

(58) Field of Classification Search
CPC combination set(s) only.
See application file for complete search history.

(56) References Cited

U.S. PATENT DOCUMENTS

| 5,776,063 A | 7/1998 | Dittrich et al. |
| 7,672,491 B2 | 3/2010 | Krishnan et al. |

(Continued)

FOREIGN PATENT DOCUMENTS

| WO | WO 2014/097090 A1 | 6/2014 |
| WO | WO 2014/155272 | 10/2014 |
| WO | WO 2017/181288 A1 | 10/2017 |

OTHER PUBLICATIONS

"2019 CES Butterfly Personal Whole Body Ultrasound," (retrieved from the Internet at YOUTUBE "2019 CES Butterfly Personal Whole Body Ultrasound," Sync Media Network https://www.youtube.com/watch?v=m21kXPUI-_g&feature=youtu.be Jan. 11, 2019).
(Continued)

*Primary Examiner* — Anand P Bhatnagar
(74) *Attorney, Agent, or Firm* — Knobbe, Martens, Olson & Bear, LLP

(57) ABSTRACT

Embodiments of a computer-implemented method of facilitating ultrasonic image analysis of a subject are disclosed. The method can involve receiving signals representing a set of ultrasound images of the subject, deriving one or more extracted feature representations from the set of ultrasound images, determining, based on the derived one or more extracted feature representations, a quality assessment value representing a quality assessment of the set of ultrasound images, determining, based on the derived one or more extracted feature representations, an image property associated with the set of ultrasound images, and producing signals representing the quality assessment value and the image property for causing the quality assessment value and the image property to be associated with the set of ultrasound images. Embodiments of a computer-implemented method of training one or more neural networks to facilitate ultrasonic image analysis is also disclosed. Other apparatuses,
(Continued)

methods, systems, and computer-readable media are also disclosed.

30 Claims, 13 Drawing Sheets

Related U.S. Application Data

(60) Provisional application No. 62/725,913, filed on Aug. 31, 2018.

(52) U.S. Cl.
CPC ............ *A61B 8/483* (2013.01); *A61B 8/5215* (2013.01); *A61B 8/466* (2013.01)

(56) References Cited

U.S. PATENT DOCUMENTS

| | | | | |
|---|---|---|---|---|
| 7,672,517 | B2* | 3/2010 | Buscema | G06T 5/20 382/162 |
| 7,680,308 | B2 | 3/2010 | Dale | |
| 7,912,528 | B2 | 3/2011 | Krishnan et al. | |
| 8,594,398 | B2 | 11/2013 | Beymer et al. | |
| 8,712,157 | B2 | 4/2014 | Marchesotti et al. | |
| 8,744,152 | B2 | 6/2014 | Beymer et al. | |
| 8,750,375 | B2 | 6/2014 | Beymer et al. | |
| 8,891,881 | B2 | 11/2014 | Gupta et al. | |
| 8,917,917 | B2 | 12/2014 | Bwymar et al. | |
| 9,652,846 | B1 | 5/2017 | Codella et al. | |
| 9,918,701 | B2* | 3/2018 | Hedlund | A61B 6/487 |
| 10,074,038 | B2* | 9/2018 | Hsieh | G06T 7/0002 |
| 10,127,659 | B2* | 11/2018 | Hsieh | G06F 19/00 |
| 10,140,734 | B2* | 11/2018 | Chen | G06T 11/00 |
| 10,242,443 | B2* | 3/2019 | Hsieh | G06N 3/04 |
| 2005/0020903 | A1* | 1/2005 | Krishnan | G16H 50/20 600/407 |
| 2005/0251013 | A1 | 11/2005 | Krishnan et al. | |
| 2006/0147107 | A1 | 7/2006 | Zhang et al. | |
| 2009/0034808 | A1 | 2/2009 | Zhou et al. | |
| 2009/0074280 | A1 | 3/2009 | Lu et al. | |
| 2009/0088640 | A1* | 4/2009 | Park | G06K 9/6257 600/453 |
| 2010/0168578 | A1 | 7/2010 | Garson, Jr. et al. | |
| 2011/0082371 | A1 | 4/2011 | Chono | |
| 2015/0086093 | A1 | 3/2015 | Fonte et al. | |
| 2015/0302638 | A1 | 10/2015 | Jago et al. | |
| 2017/0026298 | A1 | 1/2017 | Huo | |
| 2017/0143312 | A1* | 5/2017 | Hedlund | A61B 6/487 |
| 2017/0360401 | A1 | 12/2017 | Rothberg et al. | |
| 2017/0360402 | A1 | 12/2017 | De Jonge et al. | |
| 2017/0360403 | A1 | 12/2017 | Rothberg et al. | |
| 2017/0360411 | A1 | 12/2017 | Rothberg et al. | |
| 2017/0360412 | A1 | 12/2017 | Rothberg et al. | |
| 2018/0144214 | A1* | 5/2018 | Hsieh | G06K 9/6265 |
| 2018/0153505 | A1 | 6/2018 | Cadieu et al. | |
| 2018/0310920 | A1* | 11/2018 | Specht | A61B 8/5269 |
| 2019/0059851 | A1 | 2/2019 | Rothberg | |
| 2019/0104949 | A1 | 4/2019 | Cadieu et al. | |
| 2019/0125298 | A1* | 5/2019 | Abolmaesumi | G06N 3/08 |
| 2019/0130554 | A1* | 5/2019 | Rothberg | G01S 17/00 |
| 2019/0142390 | A1* | 5/2019 | Luo | A61B 8/5215 |
| 2019/0266716 | A1* | 8/2019 | Rothberg | G01S 17/00 |

OTHER PUBLICATIONS

Abdi A.H. et al., "Automatic quality assessment of echocardiograms using convolutional neural networks: Feasibility on the apical four-chamber view". Trans. Medical Imaging. 2017.

Abdi A.H. et al., "Quality assessment of echocardiographic cine using recurrent neural networks: Feasibility on five standard view planes". In Proceedings of MICCAI 2017.

"Healthcare Summit 2017: Spotlight: An Ultrasound in Your Pocket—Forbes Live," (retrieved from the Internet at YOUTUBE "Healthcare Summit 2017: Spotlight: An Ultrasound in Your Pocket—Forbes Live," Forbes Live https://www.youtube.com/watch?v=Rl-tpOXqk8k &feature=youtu.be Dec. 4, 2017).

Hochreiter S et al., "Long short-term memory". Neural computation. 1997.

Huang G. et al., "Densely connected convolutional networks". In Proceedings of the IEEE conference on CVPR. 2017.

International Search Report and Written Opinion in PCT Application No. PCT/CA2019/051192 dated Nov. 8, 2019.

Ioffe, S. et al., "Batch normalization: Accelerating deep network training by reducing internal covariate shift". In: Proceedings of the $32^{nd}$ International Conference on Machine Learning. pp. 448-456. ICML'15, JMLR (2015).

Kim J. et al, "Deep Convolutional Neural Models for Picture-Quality Prediction", IEEE Signal Processing Magazine, Nov. 13, 2017.

Lu, X. et al., "AutoMPR: Automatic detection of standard planes in 3D echocardiography". In: $5^{th}$ IEEE International Symposium on ISBI 2008, pp. 1279-1282 (2008).

Nair, V. et al., "Rectified linear units improve restricted Boltzmann machines". In: Proceedings of the $27^{th}$ international conference on machine learning ( ICML-10). pp. 807-814 (2010).

Search Strategy in PCT Application No. PCT/CA2019/051192 dated Nov. 8, 2019.

Sri-Kaushik Pavani, et al., "Quality Metric for Parasternal Long Axis B-Mode Echocardiograms," published in Medical Image Computing and Computer Assisted Intervention (MICCAI) in Jan. 2012. vol. 15, part 2, pp. 478-485.

U.S. Appl. No. 16/095,601, including its prosecution history, and the Office Actions therein, dated Oct. 22, 2018, Abolmaesumi.

Alison Noble, et al., "Ultrasound Image Segmentation: A Survey," published in IEEE Transactions on Medical maging from the Institute of Electrical and Electronics Engineers in Aug. 2006. vol. 25, issue 8, pp. 87-1010.

A.S. Miller, et al., "Review of Neural Network Applications in Medical Imaging and Signal Processing," published in Medical & Biological Engineering & Computing in Sep. 1992. vol. 30, pp. 449-464.

Canadian Intellectual Property Office, International Search Report and Written Opinion of the international Searching Authority in PCT/CA2017/050496, dated Jul. 13, 2017, which is the international application to this U.S. application.

Curt G. Degroff, MD; et al., "Artificial Neural Network-Based Method of Screening Heart Murmurs in Children," published in Circulation by the American Heart Association on Jun. 5, 2001. vol. 103, issue 22, pp. 2711-2716.

Dipti Itchhaporia, MD; et al., "Artificial Neural Networks: Current Status in Cardiovascular Medicine," published in the Journal of the American College of Cardiology (JACC) in Aug. 1996. vol. 28, issue 2, pp. 515-521.

Hao Chen, et al., "Iterative Multi-domain Regularized Deep Learning for Anatomical Structure Detection and Segmentation from Ultrasound Images," submitted to Medical Image Computing and Computer Assisted Intervention, Dart 2 (MICCAI) in Jul. 2016.

Hoo-Chang Shin, et al., "Deep Convolutional Neural Networks for Computer-Aided Detection: CNN Architectures, Dataset Characteristics and Transfer Learning," submitted to hllps://www.arXiv.org on Feb. 10, 2016.

J. Jiang, et al., "Medical Imaging Analysis with Artificial Neural Networks," published in Computerized Medical Imaging and Graphics in 2010. vol. 34, issue 8, pp. 617-631.

Neelam Sinha, et al., "Quality Assessment in Magnetic Resonance Images," published in Critical Reviews™ in Biomedical Engineering {CRMBE) in 2010. vol. 38, issue 2, pp. 127-141.

Nima Torbati, et al., "An Efficient Neural Network Based Method for Medical Image Segmentation," published in computers in Biology and Medicine by Elsevier on Jan. 1, 2014. vol. 44, pp. 76-87.

Noha El-Zehiry, et al., "Learning the Manifold of Quality Ultrasound Acquisition," published in Medical Image computing and Computer Assisted Intervention, Part 1 (MCCAiI) in Sep. 2013.

Nov. 8, 2019, Extended European Search Report from the European Patent Office in European Patent Application Serial No. 17785210. 0, which is a foreign counterpart to this application.

(56) References Cited

OTHER PUBLICATIONS

R.H. Clayton, et al., "Recognition of Ventricular Fibrillation Using Neural Networks," published in Medical & Biological Engineering & Computing in Mar. 1994. vol. 32, pp. 217-220.

S. Kevin Zhou, et al., "Image-based Multiclass Boosting and Echocardiographic View Classification," in 2006 IEEE computer Society Conference on Computer Vision and Pattern Recognition {CVPR'06). vol. 2, pp. 1559-1565.

Shijun Wang, et al., "Machine Learning and Radiology," published in Medical Image Analysis by Elsevier in Jul. J012. vol. 16, issue 5, pp. 993-951.

Sri-Kaushik Pavani, et al., "Quality Metric for Parasternal Long Axis B-Mode Echocardiograms," published in Medical Image Computing and Computer Assisted Intervention {MICCAI) in Jan. 2012. vol. 15, part 2, pp. 178-485.

Sten Roar Snare, et al., "Real-Time Scan Assistant for Echocardiography," in IEEE Transactions on Ultrasonics, Ferroelectrics, and Frequency Control in Mar. 2012. vol. 59, issue 3, pp. 583-589.

Timothy J_ W. Dawes, FRCA, PhD; et al., "Machine Learning of Three-dimensional Right Ventricular Motion Enables Outcome Prediction in Pulmonary Hypertension: A Cardiac MR Imaging Study," published online in Radiology n Jan. 2017.

Xiaoguang Lu, et al., "AutoMPR: Automatic Detection of Standard Planes in 3D Echocardiography," published in J008 5th IEEE International Symposium on Biomedical Imaging: From Nano to Macro in Jun. 2008. pp. 1279-1282.

Xiaoming Liu, et al., "Learning-based Scan Plane Identification from Fetal Head Ultrasound Images," published in Medical Imaging 2012: Ultrasonic Imaging, Tomography, and Therapy; 83200A in Feb. 2012. Proceedings SPIE vol. 8320.

Amir, et al., "Automatic quality assessment of apical four-chamber echocardiograms using deep convolutional neural networks," Proc. of SPIE vol. 10133, downloaded Mar. 9, 2020, 8 pages.

Abdi, et al., "Automatic quality assessment of apical four-chamber echocardiograms using deep convolutional neural networks," Medical Imaging 2017: Image Processing, edited by Martin A. Styner, Elsa D. Angelini, Proc. of SPIE, vol. 10133, 101330S, Feb. 2017, 8 pages.

International Search Report dated Nov. 8, 2019 for Application No. PCT/CA2019/051192, 3 pages.

Written Opinion of the International Searching Authority dated Nov. 8, 2019 for Application No. PCT/CA2019/051192, 5 pages.

\* cited by examiner

ULTRASONIC IMAGE ANALYSIS

RELATED APPLICATION

This application is a continuation of International Application No. PCT/CA2019/051192, filed on Aug. 28, 2019, and claims the benefit of U.S. Provisional Application No. 62/725,913 entitled "ULTRASONIC IMAGE ANALYSIS", filed on Aug. 31, 2018, both of which are hereby incorporated by reference herein in their entirety.

BACKGROUND

1. Field

Embodiments of this disclosure relate to ultrasonic image analysis and more particularly to ultrasonic image analysis for determining image quality and image properties.

2. Description of Related Art

Accurate diagnosis in ultrasound requires high quality ultrasound images, which may need to show or contain different specific features and structures depending on various properties of the images. Some ultrasound systems may not provide feedback to operators regarding quality of the image and/or other image properties. Inexperienced ultrasound operators may have a great deal of difficulty using such known systems to recognize features in the ultrasound images and thus can fail to capture diagnostically relevant ultrasound images.

SUMMARY

In accordance with various embodiments, there is provided a computer-implemented method of facilitating ultrasonic image analysis of a subject. The method involves receiving signals representing a set of ultrasound images of the subject, deriving one or more extracted feature representations from the set of ultrasound images, determining, based on the derived one or more extracted feature representations, a quality assessment value representing a quality assessment of the set of ultrasound images, determining, based on the derived one or more extracted feature representations, an image property associated with the set of ultrasound images, and producing signals representing the quality assessment value and the image property for causing the quality assessment value and the image property to be associated with the set of ultrasound images.

The image property may be a view category.

Deriving the one or more extracted feature representations from the ultrasound images may involve, for each of the ultrasound images, deriving a first feature representation associated with the ultrasound image.

Deriving the one or more extracted feature representations may involve, for each of the ultrasound images, inputting the ultrasound image into a commonly defined first feature extracting neural network to generate the first feature representation associated with the ultrasound image.

Deriving the one or more extracted feature representations may involve concurrently inputting each of a plurality of the ultrasound images into a respective implementation of the commonly defined first feature extracting neural network.

The commonly defined first feature extracting neural network may include a convolutional neural network.

Deriving the one or more extracted feature representations may involve inputting the first feature representations into a second feature extracting neural network to generate respective second feature representations, each associated with one of the ultrasound images. The one or more extracted feature representations may include the second feature representations.

The second feature extracting neural network may be a recurrent neural network.

Determining the quality assessment value may involve inputting the one or more extracted feature representations into a quality assessment value specific neural network and determining the image property may involve inputting the one or more extracted feature representations into an image property specific neural network.

Inputting the one or more extracted feature representations into the quality assessment value specific neural network may involve inputting each of the one or more extracted feature representations into an implementation of a commonly defined quality assessment value specific neural subnetwork and inputting the one or more extracted feature representations into the image property determining neural network may involve inputting each of the one or more extracted feature representations into an implementation of a commonly defined image property specific neural network.

Producing signals representing the quality assessment value and the image property for causing the quality assessment value and the image property to be associated with the set of ultrasound images may involve producing signals for causing a representation of the quality assessment value and a representation of the image property to be displayed by at least one display in association with the set of ultrasound images.

In accordance with various embodiments, there is provided a computer-implemented method of training one or more neural networks to facilitate ultrasonic image analysis. The method involves receiving signals representing a plurality of sets of ultrasound training images, receiving signals representing quality assessment values, each of the quality assessment values associated with one of the sets of ultrasound training images and representing a quality assessment of the associated set of ultrasound training images, receiving signals representing image properties, each of the image properties associated with one of the sets of ultrasound training images, and training a neural network, the training comprising, for each set of the plurality of sets of ultrasound training images, using the set of ultrasound training images as an input to the neural network and using the quality assessment values and the image properties associated with the set of ultrasound training images as desired outputs of the neural network.

Each of the image properties may be a view category.

The neural network may include a feature extracting neural network, an image property specific neural network, and a quality assessment value specific neural network. The feature extracting neural network may be configured to take an input set of the plurality of sets of ultrasound training images as an input and to output one or more extracted feature representations. The image property specific neural network may be configured to take the one or more extracted feature representations as an input and to output a representation of an image property associated with the input set of ultrasound training images. The quality assessment specific neural network may be configured to take the one or more extracted feature representations as an input and to output a quality assessment value associated with the input set of ultrasound training images.

The feature extracting neural network may be configured to, for each of the ultrasound training images included in the input set of ultrasound training images, derive a first feature representation associated with the ultrasound image.

The feature extracting neural network may include, for each of the ultrasound images included in the input set of ultrasound training images, a commonly defined first feature extracting neural network configured to take as an input the ultrasound training image and to output a respective one of the first feature representations.

More than one implementation of the commonly defined first feature extracting neural networks may be configured to concurrently generate the first feature representations.

The commonly defined first feature extracting neural network may be a convolutional neural network.

The feature extracting neural network may include a second feature extracting neural network configured to take as an input the first feature representations and to output respective second feature representations, each associated with one of the ultrasound images included in the input set of ultrasound training images and the one or more extracted feature representations may include the second feature representations.

The second feature extracting neural network may be a recurrent neural network.

In accordance with various embodiments, there is provided a system for facilitating ultrasonic image analysis including at least one processor configured to perform any of the above methods.

In accordance with various embodiments, there is provided a non-transitory computer readable medium having stored thereon codes which when executed by at least one processor cause the at least one processor to perform any of the above methods.

In accordance with various embodiments, there is provided a system for facilitating ultrasonic image analysis, the system including means for receiving signals representing a set of ultrasound images of the subject, means for deriving one or more extracted feature representations from the set of ultrasound images, means for determining, based on the derived one or more extracted feature representations, a quality assessment value representing a quality assessment of the set of ultrasound images, means for determining, based on the derived one or more extracted feature representations, an image property associated with the set of ultrasound images, and means for producing signals representing the quality assessment value and the image property for causing the quality assessment value and the image property to be associated with the set of ultrasound images. In accordance with various embodiments, there is provided a system for training one or more neural networks to facilitate ultrasonic image analysis, the system including means for receiving signals representing a plurality of sets of ultrasound training images, means for receiving signals representing quality assessment values, each of the quality assessment values associated with one of the sets of ultrasound training images and representing a quality assessment of the associated set of ultrasound training images, means for receiving signals representing image properties, each of the image properties associated with one of the sets of ultrasound training images, and means for training a neural network, the training comprising, for each set of the plurality of sets of ultrasound training images, using the set of ultrasound training images as an input to the neural network and using the quality assessment values and the image properties associated with the set of ultrasound training images as desired outputs of the neural network.

Other aspects and features of embodiments of the disclosure will become apparent to those ordinarily skilled in the art upon review of the following description of specific embodiments of the disclosure in conjunction with the accompanying figures.

BRIEF DESCRIPTION OF THE DRAWINGS

In drawings which illustrate embodiments of the disclosure.

DETAILED DESCRIPTION

Figure 1:
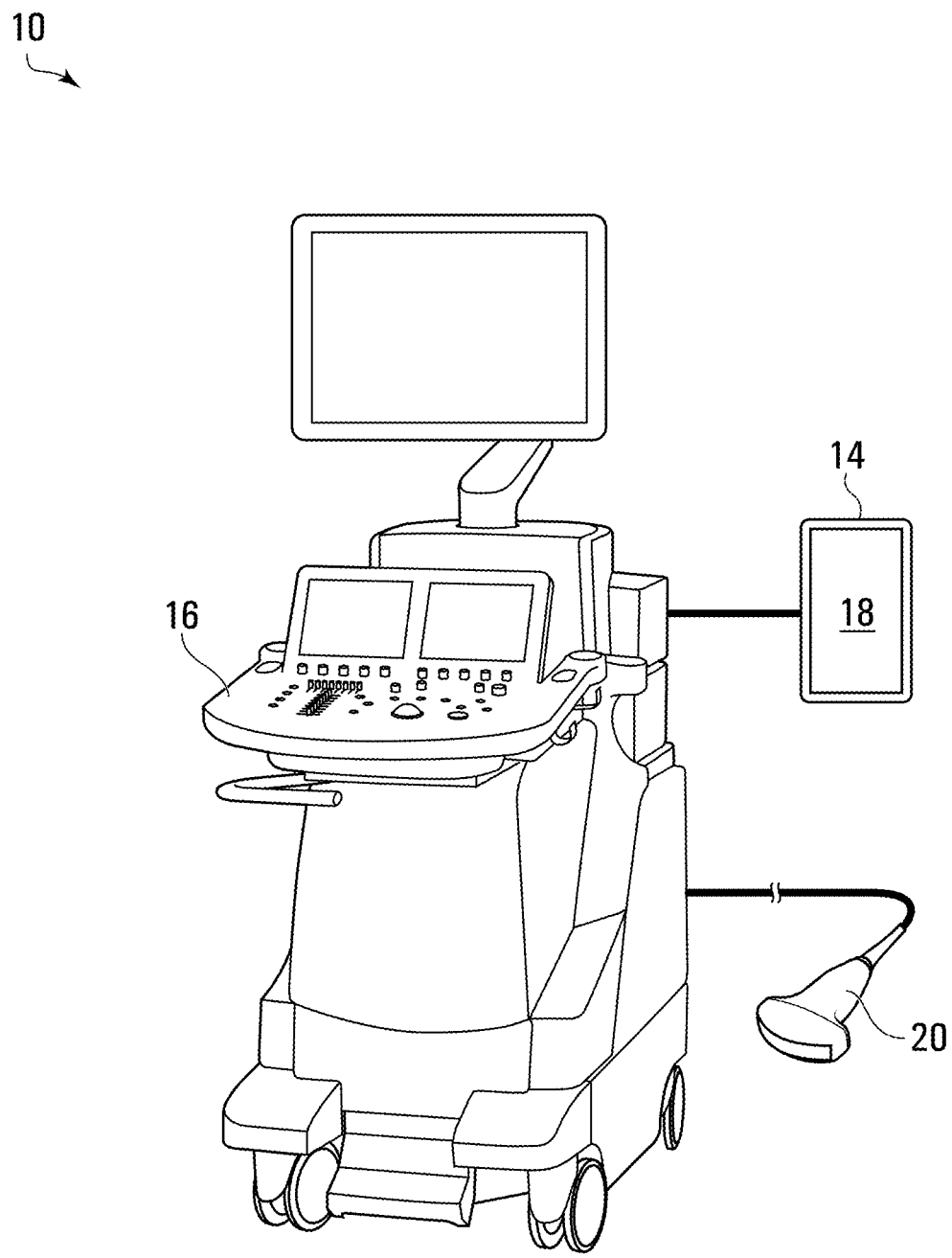
FIG. 1 is a schematic view of a system for facilitating ultrasonic image analysis of a subject according to various embodiments of the disclosure.

Referring to FIG. 1, there is provided a system 10 for facilitating ultrasonic image analysis of a subject according to various embodiments. The system 10 includes a computer-implemented image analyzer 14 in communication with an ultrasound machine 16 having a transducer 20. In various embodiments, the analyzer 14 may include a display 18. In some embodiments, the analyzer 14 may be implemented as a mobile device, for example.

In various embodiments, the system 10 may provide feedback to an operator of the ultrasound machine 16 regarding quality of the ultrasound images being captured and other image properties. For example, in some embodiments, the system 10 may provide real-time or near real-time feedback to the operator in the form of a view category or classification and image quality estimation. In various embodiments, this may allow the operator to capture ultrasound images that facilitate more accurate analysis, which may in some embodiments allow more accurate diagnosis of a patient acting as the subject of the analysis.

In some embodiments, for example, by providing real-time or near real-time feedback to the operator, the system 10 may be used to facilitate capturing high quality images for cardiac ultrasound imaging wherein specific features and structures may need to be imaged. The required features and structures in cardiac ultrasound imaging may depend on which of the 14 standard cardiac views the operator is attempting to acquire and so real-time or near real-time feedback that provides both a quality assessment value and a view category for the images the operator is capturing may be particularly helpful. In some embodiments, by providing real-time or near real-time feedback to the operator, the system 10 may allow inexperienced operators to more easily recognize the specific features and structures required of various views and thus the system 10 may be able to capture diagnostically relevant sets of ultrasound images or heart cines.

In various embodiments, the system 10 may be particularly useful because some of the view categories for ultrasound imaging may be quite similar to an inexperienced eye and switching between them may require precise adjustments of the probe's position and orientation. In various embodiments, the system 10 may reduce the adverse effect of inter-operator variability on the quality of the acquired ultrasound images. In some embodiments, the system 10 may do this by providing the operator with real-time or near real-time feedback of both view classification and image quality.

In various embodiments, this may be done through the use of a deep learning neural network, which may, for example, be capable of simultaneously determining which view category of fourteen (14) possible view categories the captured images fall into and determining a quality assessment value acting as a quality estimation score. In various embodiments, the architecture of the neural network implemented by the analyzer 14 may allow the analyzer to be implemented by a device that does not require an extremely high computing power, such as, for example an application on a mobile device or running on an off-the-shelf mobile device with the result being that the analyzer 14 may be portable and/or cost effective. In some embodiments, by combining quality assessment and another image property assessment, such as view categorization, a highly shared neural network may yield faster processing time compared to using a separate quality assessment and image property assessment, such as view categorization. In some embodiments, by combining quality assessment and another image property assessment, such as view categorization, the joint training of the two modalities may prevent the neural network from overfitting the label from either modality. In some embodiments, by combining quality assessment and another image property assessment, such as view categorization, there may be cost savings since a single model needs to be maintained rather than multiple separate models.

Referring now to FIG. 1, use of the system 10 will be discussed in accordance with various embodiments. In use, the ultrasound machine 16 and transducer 20 may be controlled by an operator to send and receive ultrasound signals to and from the subject via the transducer 20, to produce ultrasound image representations of the subject. For example, in some embodiments, the subject may be a person or patient. In some embodiments, the transducer 20 may be manipulated such that the ultrasound machine 16 produces ultrasound images of a heart of the person, for example.

In some embodiments, a representation of the ultrasound images may be transmitted to the analyzer 14. In some embodiments, the system 10 may include a frame grabber configured to capture raw video output from the ultrasound machine 16 and to transmit a serial data stream representing a set of ultrasound images to the analyzer 14. For example, in some embodiments, the frame grabber may be configured to receive its input directly from a DVI port of the ultrasound machine 16, using an Epiphan AV.IO frame grabber, for example, to capture and convert the raw video output to a serial data stream. In some embodiments, the frame grabber output may be adapted from USB-A to USB-C with an On-The-Go (OTG) adapter, allowing the frame grabber to pipe video output from the ultrasound machine 16 directly into the analyzer 14. As described below, the analyzer 14 may run or implement a neural network which is configured to process the video output received from the frame grabber. In some embodiments, the analyzer 14 may use TensorFlow Java inference interface, for example.

In some embodiments, referring to FIG. 1, the analyzer 14 may receive signals representing a set of ultrasound images of the subject. For example, in various embodiments, the analyzer 14 may receive ultrasound images from a frame grabber in communication with the ultrasound machine 16 and the analyzer 14. In various embodiments, the set of ultrasound images received may represent a video or cine and may be a temporally ordered set of ultrasound images. In some embodiments, the set of ultrasound images received may represent an echocardiographic cine, for example, showing a patient's heart over time.

The analyzer 14 may then derive one or more extracted feature representations from the received set of ultrasound images. In some embodiments, the analyzer 14 may implement a neural network including a feature extracting neural network and the analyzer 14 may input the set of ultrasound images into the feature extracting neural network in order to derive the one or more extracted feature representations.

The analyzer 14 may then determine, based on the derived one or more extracted feature representations, a quality assessment value representing a quality assessment of the set of ultrasound images. In some embodiments, the analyzer 14 may input the one or more extracted feature representations into a quality assessment value specific neural network in order to determine the quality assessment value. In some embodiments, a neural network including the feature extracting neural network and the quality assessment specific neural network may have been previously trained such that the quality assessment value determined by the analyzer 14 may represent an assessment of suitability of the received set of ultrasound images for quantified clinical measurement of anatomical features.

The analyzer 14 may also determine, based on the derived one or more extracted feature representations, an image property associated with the set of ultrasound images. In some embodiments, the image property may be a view category, for example. Accordingly, in some embodiments, the analyzer 14 may input the one or more extracted feature representations into a view category specific neural network in order to determine a view category within which the set of ultrasound images are determined to fall. In some embodiments, the neural network including the feature extracting neural network and the view category specific neural network may have been previously trained such that the view category determined by the analyzer 14 may represent the category of view represented by the set of ultrasound images.

The analyzer 14 may then produce signals representing the quality assessment value and the image property for causing the quality assessment value and the image property to be associated with the set of ultrasound images. In some embodiments, the analyzer 14 may produce signals for causing a representation of the quality assessment value and a representation of the view category to be displayed by the display 18 in association with the set of ultrasound images. For example, the classified view and its associated quality score may be displayed in a graphical user interface (GUI) on the display 18 as feedback to the operator.

In various embodiments, this near real-time or real-time feedback to the operator may help the operator improve their skills and/or improve image quality for subsequently captured images. For example, in some embodiments, the operator may, in response to viewing a low-quality assessment value or undesired view category on the display 18, adjust positioning of the transducer and/or adjust image capture parameters, such as, for example, depth, focus, gain, frequency, and/or another parameter which may affect image quality, and/or the view category of the images being captured. In some embodiments, the operator may make such adjustments until a high-quality assessment value and/or a desired view category is displayed by the display 18, for example, at which point the operator may be confident that the images captured are suitable for subsequent quantified clinical measurement of anatomical features and/or to assist in diagnosing a medical condition of the subject, for example.

In some embodiments, the analyzer 14 may produce signals representing the quality assessment value and the image property in association with the set of ultrasound images for facilitating automatic adjustment, using another neural network or machine learning, of image capture parameters to maximize quality assessment values. For example, in some embodiments, another neural network may use the quality assessment value and image property as inputs for generating control signals for adjusting image capture parameters to maximize quality assessment values.

Analyzer—Processor Circuit

Figure 2:
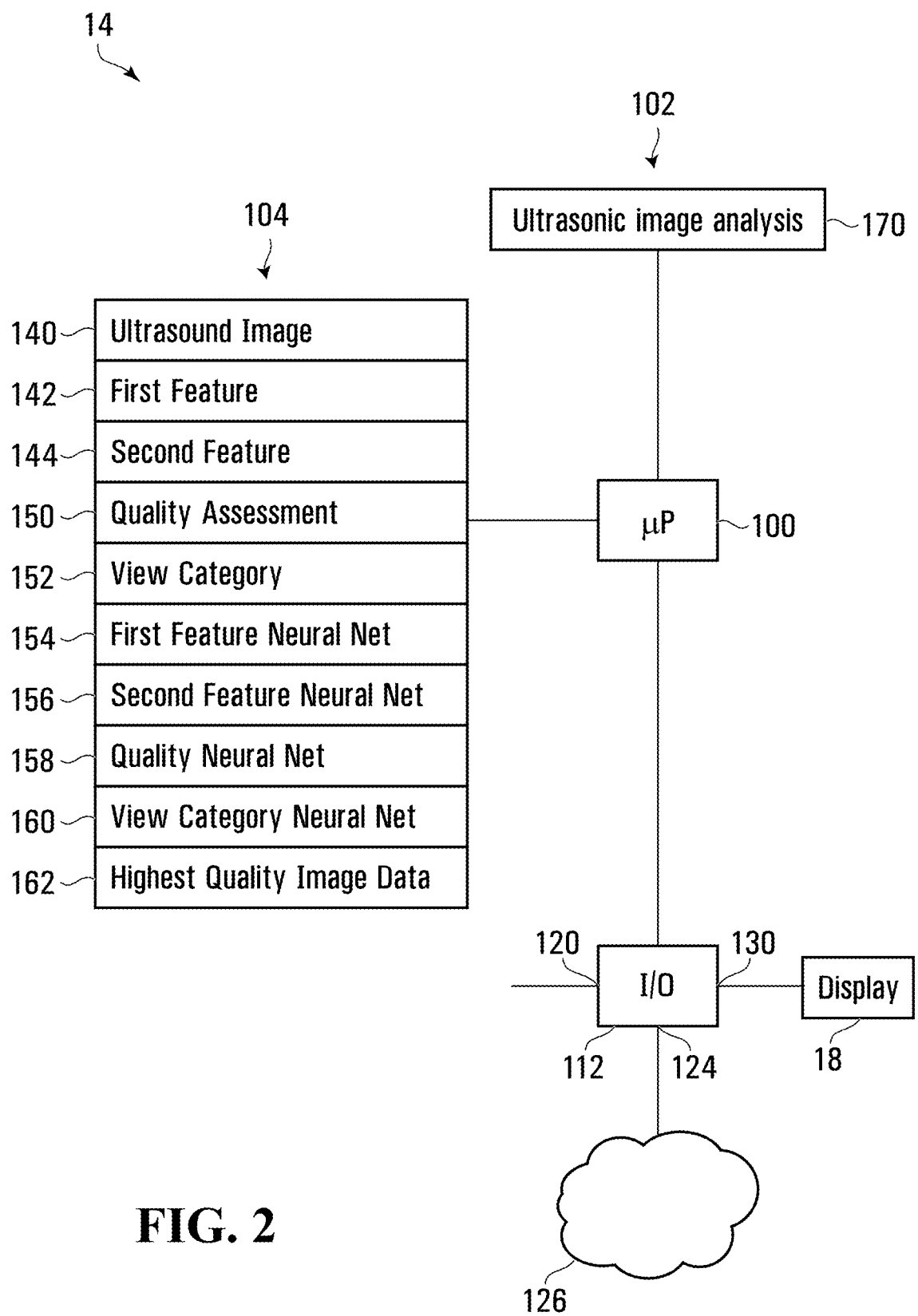
FIG. 2 is a schematic view of an image analyzer of the system shown in FIG. 1 including a processor circuit in accordance with various embodiments of the disclosure.

Referring now to FIG. 2, a schematic view of the analyzer 14 of the system 10 shown in FIG. 1 according to various embodiments is shown. In various embodiments, the analyzer 14 may be implemented as a mobile device, such as a Samsung™ Galaxy S8+™ running an operating system, such as Android™, for example.

Referring to FIG. 2, the analyzer 14 includes a processor circuit including an analyzer processor 100 and a program memory 102, a storage memory 104, and an input/output (I/O) interface 112, all of which are in communication with the analyzer processor 100. In various embodiments, the analyzer processor 100 may include one or more processing units, such as for example, a central processing unit (CPU), a graphical processing unit (GPU), and/or a field programmable gate array (FPGA). In some embodiments, any or all of the functionality of the analyzer 14 described herein may be implemented using one or more FPGAs.

The I/O interface 112 includes an interface 120 for communicating with the ultrasound machine 16 or a frame grabber in communication with the ultrasound machine 16 and an interface 130 for communicating with the display 18. In some embodiments, the I/O interface 112 may also include an interface 124 for facilitating networked communication through a network 126. In some embodiments, any or all of the interfaces 120, 130, or 124 may facilitate a wireless or wired communication.

In some embodiments, the I/O interface 112 may include a network interface device or card with an input/output for connecting to the network 126, through which communications may be conducted with devices connected to the network 126, such as the neural network trainer (as shown at 502 in FIG. 11), for example. In some embodiments, the network 126 may be a private network to which both the analyzer 14 and the trainer 502 are connected. In some embodiments the network 126 may be a public network, such as the Internet, for example.

In some embodiments, each of the interfaces shown in FIG. 2 may include one or more interfaces and/or some or all of the interfaces included in the I/O interface 112 may be implemented as combined interfaces or a single interface.

In some embodiments, where a device is described herein as receiving or sending information, it may be understood that the device receives signals representing the information via an interface of the device or produces signals representing the information and transmits the signals to the other device via an interface of the device.

Processor-executable program codes for directing the analyzer processor 100 to carry out various functions are stored in the program memory 102. Referring to FIG. 2, the program memory 102 includes a block of codes 170 for directing the analyzer 14 to perform ultrasound image analysis functions. In this specification, it may be stated that certain encoded entities such as applications or modules perform certain functions. Herein, when an application, module or encoded entity is described as taking an action, as part of, for example, a function or a method, it will be understood that at least one processor (e.g., the analyzer processor 100) is directed to take the action by way of programmable codes or processor-executable codes or instructions defining or forming part of the application.

The storage memory 104 includes a plurality of storage locations including location 140 for storing ultrasound image data, location 142 for storing first extracted feature data, location 144 for storing second extracted feature data, location 150 for storing determined quality assessment value data, location 152 for storing determined view category data, location 154 for storing first feature extracting neural network parameter data, location 156 for storing second feature extracting neural network parameter data, location 158 for storing quality assessment value specific neural network parameter data, location 160 for storing view category specific neural network parameter data, and location 162 for storing highest quality image data. In various embodiments, the plurality of storage locations may be stored in a database in the storage memory 104.

In various embodiments, the block of codes 170 may be integrated into a single block of codes or portions of the block of codes 170 may include one or more blocks of code stored in one or more separate locations in the program memory 102. In various embodiments, any or all of the locations 140, 142, 144, 150, 152, 154, 156, 158, 160, and 162 may be integrated and/or each may include one or more separate locations in the storage memory 104.

Each of the program memory 102 and storage memory 104 may be implemented as one or more storage devices including random access memory (RAM), a hard disk drive (HDD), a solid-state drive (SSD), a network drive, flash memory, a memory stick or card, any other form of non-transitory computer-readable memory or storage medium, and/or a combination thereof. In some embodiments, the program memory 102, the storage memory 104, and/or any portion thereof may be included in a device separate from the analyzer 14 and in communication with the analyzer 14 via the I/O interface 112, for example.

In various embodiments, other device components described herein, such as memory, program memory, blocks of code, storage memory, locations in memory, and/or I/O interfaces, may be implemented generally similarly to as described above for the analyzer 14.

Figure 3:
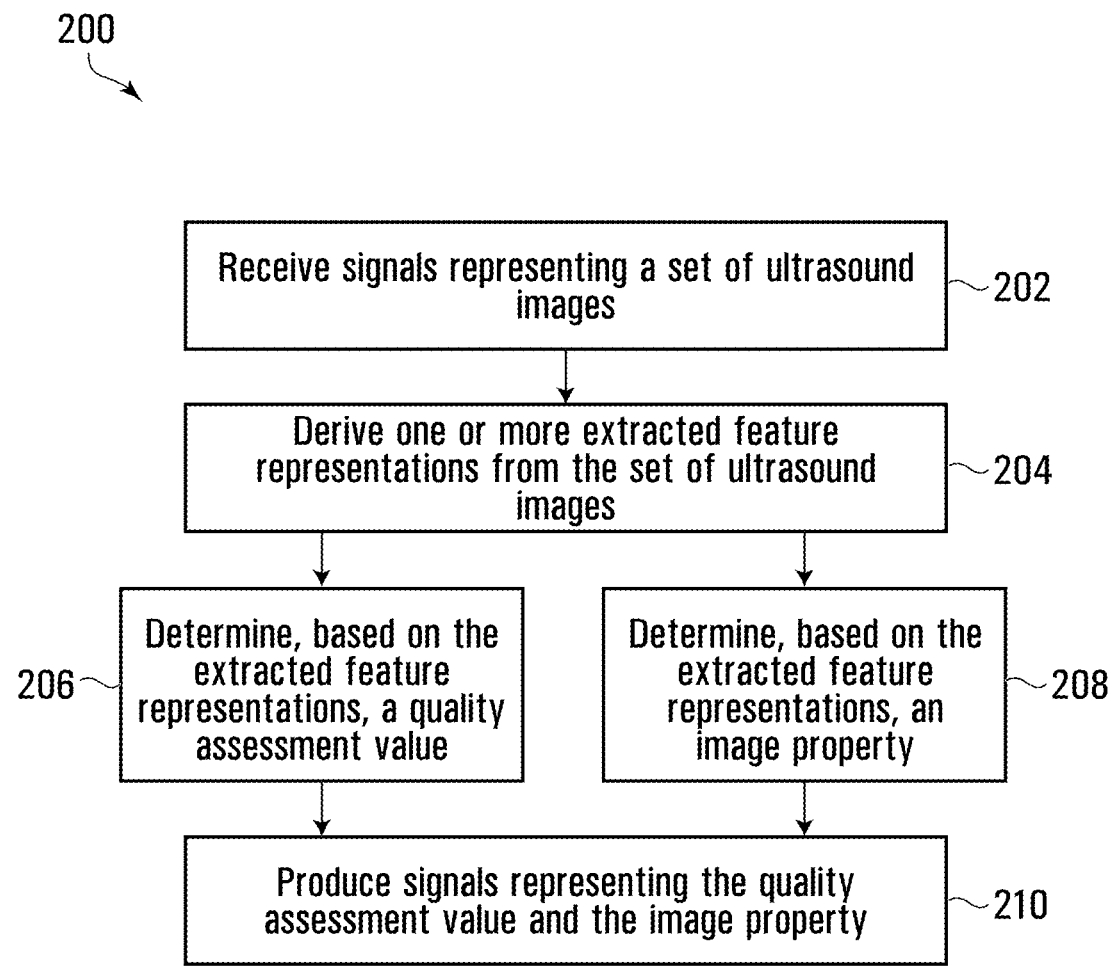
FIG. 3 is a flowchart depicting blocks of code for directing the analyzer of the system shown in FIG. 1 to perform image analysis functions in accordance with various embodiments of the disclosure.

Image analysis Referring now to FIG. 3, a flowchart depicting blocks of code for directing the analyzer processor 100 shown in FIG. 2 to perform ultrasonic image analysis functions in accordance with various embodiments is shown generally at 200. The blocks of code included in the flowchart 200 may be encoded in the block of codes 170 of the program memory 102 shown in FIG. 2 for example.

Referring to FIG. 3, the flowchart 200 begins with block 202 which directs the analyzer processor 100 shown in FIG. 2 to receive signals representing a set of ultrasound images of a subject. In various embodiments, block 202 may direct the analyzer processor 100 to receive the set of ultrasound images from the ultrasound machine 16 and to store the received set of ultrasound images in the location 140 of the storage memory 104. In some embodiments, block 202 may direct the analyzer processor 100 to receive the set of ultrasound images from a frame grabber in communication with the ultrasound machine 16 and the analyzer 14. In some embodiments, the set of ultrasound images may be a temporally ordered set of ultrasound images representing a video or cine of the subject. In some embodiments, the subject may be a heart of a patient and the set of ultrasound images may be referred as an echocine. Each image of the set of ultrasound images may be referred to herein as a frame.

In some embodiments, block 202 may direct the analyzer processor 100 to pre-process raw ultrasound images received from the ultrasound machine 16 and/or to select a subset of the ultrasound images received from the ultrasound machine 16 as the set of ultrasound images to be analyzed. For example, in some embodiments, block 202 may direct the analyzer processor 100 to receive raw ultrasound images at a resolution of 640×480 at 30 Hz. Block 202 may direct the analyzer processor 100 to crop the raw frames down to include only the ultrasound beam, the boundaries of which may be adjustable by the user. The cropped data may be resized down to 120×120 to match input dimensions of the neural network implemented by the analyzer 14. In some embodiments, block 202 may direct the analyzer processor 100 to perform a simple contrast enhancement step to mitigate quality degradation introduced by the frame grabber.

In some embodiments, block 202 may direct the analyzer processor 100 to store a subset of the received ultrasound images in the location 140 of the storage memory 104. For example, in some embodiments, block 202 may direct the analyzer processor 100 to store ten 120×120 ultrasound images in the location 140 of the storage memory 104 and those ten ultrasound images may act as the received set of ultrasound images. In some embodiments, block 202 may direct the analyzer processor 100 to store the most recent ultrasound images in the location 140 of the storage memory 104. In some embodiments, a copy of the full-resolution data may also be stored in the storage memory 104 for later expert evaluation.

Referring to FIG. 3, after block 202 has been executed, the flowchart continues to block 204. In various embodiments, execution of blocks 204, 206 and 208 of the flowchart 200 may result in the analyzer processor 100 being directed to input the received set of ultrasound images into a neural network 300 shown in FIG. 4, to generate an output of a quality assessment value and an image property, which in some embodiments may be a view category. The parameters defining the neural network 300 may be stored in the storage memory 104 and may have been previously determined during neural network training, which is described in further detail in accordance with various embodiments below.

Referring to FIG. 3, block 204 directs the analyzer processor 100 to derive one or more extracted feature representations from the set of ultrasound images received at block 202. In some embodiments, deriving the one or more extracted feature representations may involve deriving a first feature representation and then deriving a second feature representation based on the first feature representation for each ultrasound image.

In various embodiments, block 204 may direct the analyzer processor to, for each of the set of ultrasound images stored in the location 140 of the storage memory 104, derive a first feature representation associated with the ultrasound image. In some embodiments, block 204 may direct the analyzer processor 100 to derive the first feature representations by inputting each image of the set of ultrasound images (shown at 302 in FIG. 4) into a commonly defined first feature extracting neural network, instances of which are shown at 304, 306, and 308 of the neural network 300 shown in FIG. 4, for example. In some embodiments, block 204 may direct the analyzer processor 100 to input each of the ten ultrasound images stored in the location 140 of the storage memory 104 into one of the commonly defined first feature extracting neural networks 304, 306, and 308.

In some embodiments parameters defining the commonly defined first feature extracting neural network may be stored in the location 154 of the storage memory 104 and block 204 may direct the analyzer processor 100 to retrieve the parameters from the location 154 of the storage memory 104. In various embodiments, because the first feature extracting neural networks (e.g., 304, 306, and 308) are commonly defined, this may save memory in the storage memory 104.

In some embodiments, the commonly defined first feature extracting neural networks (e.g., 304, 306, and 308) may include convolutional neural networks. For example, in some embodiments, each of the neural networks 304, 306, and 308 may be implemented as a seven-layer DenseNet model as described in Huang, G., Liu, Z., Weinberger, K. Q., van der Maaten, L.: Densely connected convolutional networks. In: IEEE CVPR. vol. 1-2, p. 3 (2017). In some embodiments, the DenseNet model implementing the commonly defined first feature extracting neural networks 304, 306, and 308 may use the following hyper-parameters. First, the DenseNet may have one convolution layer with sixteen 3×3 filters, which turns gray-scale (1-channel) input images to sixteen channels. Then, the DenseNet may stack three dense blocks, each followed by a dropout layer and an average-pooling layer with filter size of 2×2. In various embodiments, after the third dense block, the average-pooling layer may be applied before the dropout layer. Each dense block may have exactly one dense-layer, which may include a sequence of batch-normalization layer (as per Ioffe, S., Szegedy, C.: Batch normalization: Accelerating deep network training by reducing internal covariate shift. In: Proceedings of the 32nd International Conference on Machine Learning. pp. 448-456. ICML'15, JMLR (2015), for example), a Rectified Linear layer (ReLU) (as per Nair, V., Hinton, G. E.: Rectified linear units improve restricted boltzmann machines. In: Proceedings of the 27th international conference on machine learning (ICML-10). pp. 807-

814 (2010), for example), a 2D convolution layer with 3×3 filters, a dropout layer, a concatenation layer, another 2D convolution layer, another dropout layer, and an average pooling layer.

A batch normalization layer may first normalize the input features by the mean and standard deviation of the features themselves. For each channel (the second dimension) of input, the features from all training samples within a mini-batch may be jointly used to compute the mean and standard deviation values, hence the name batch normalization. After the normalization, the features may be rescaled and shifted by a linear transformation operation. A ReLU activation layer may be used to provide a non-linear transformation to the features. The ReLU activation function is noted as:

$$\text{ReLU}(x)=\max(0,x),$$

Where x denotes any single element of the input feature vector. A concatenation layer may concatenate features at a given dimension, where in this case, the features may be concatenated at the channel (the second) dimension. A dropout layer may omit a percentage of feature values according to a given value between 0 and 1, which is a regularization technique to reduce overfitting towards the training data.

Figure 5:
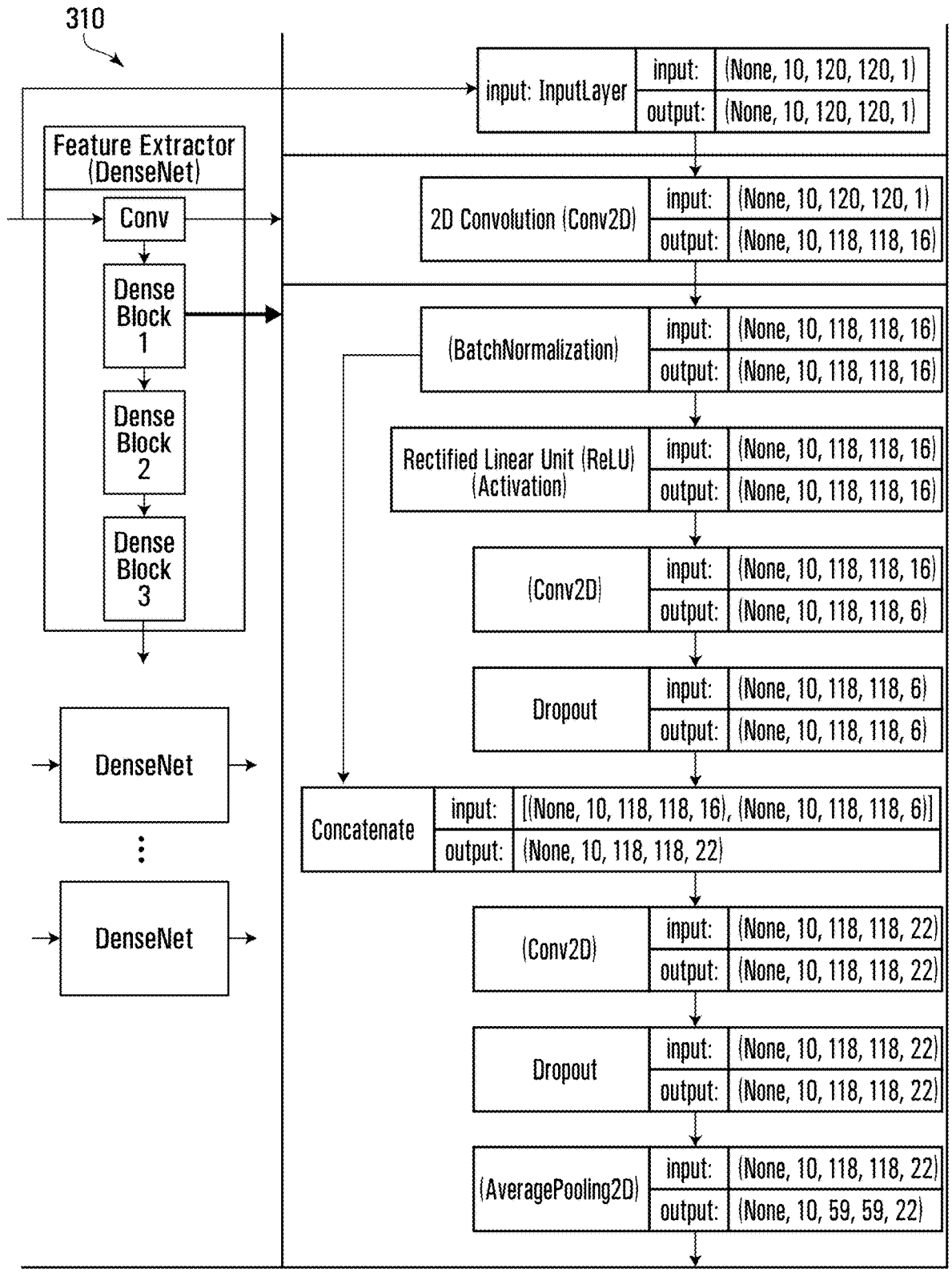
FIG. 5 is a representation of part of the neural network shown in FIG. 4 in accordance with various embodiments of the disclosure.
Figure 6:
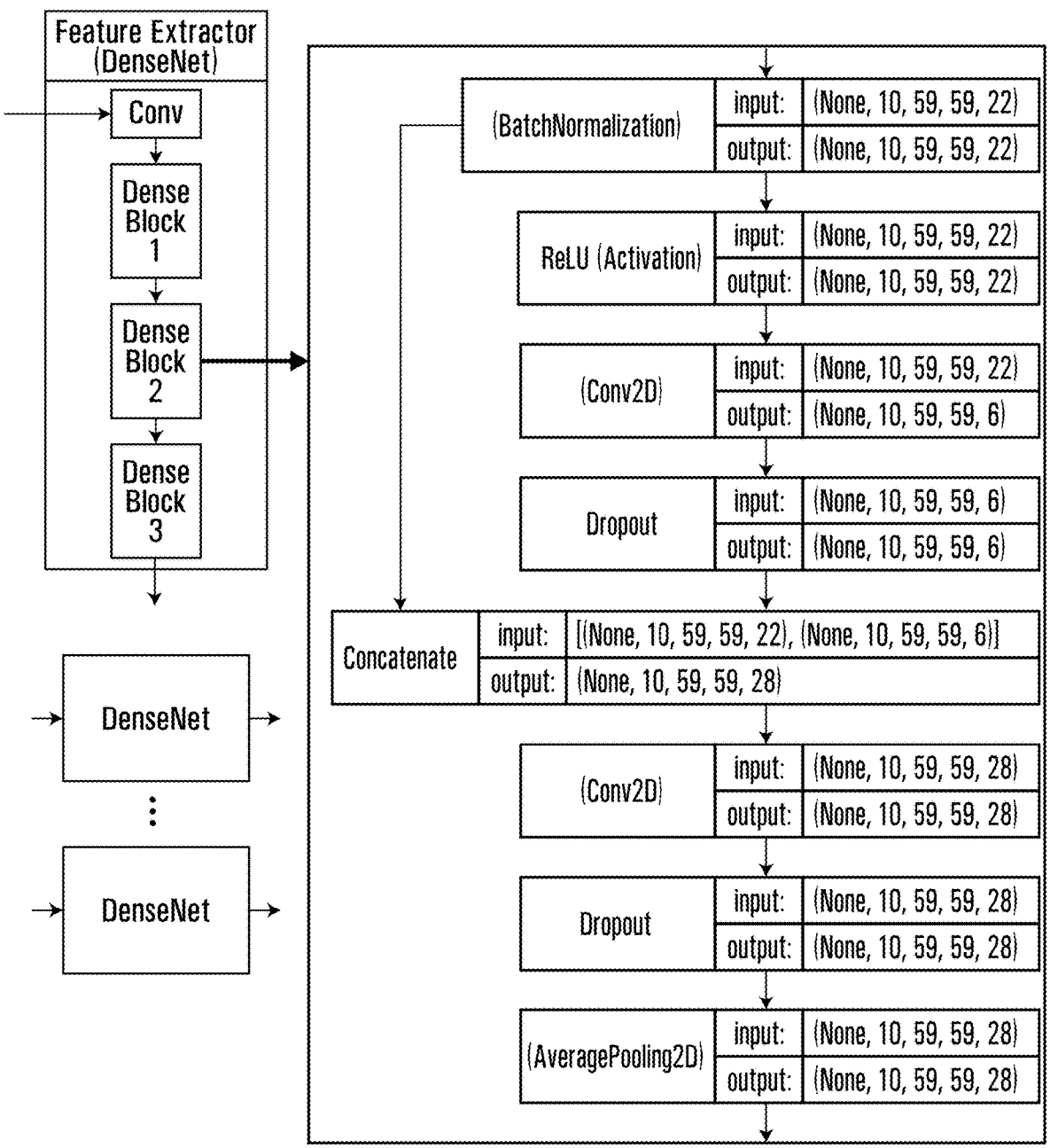
FIG. 6 is a representation of part of the neural network shown in FIG. 4 in accordance with various embodiments of the disclosure.
Figure 7:
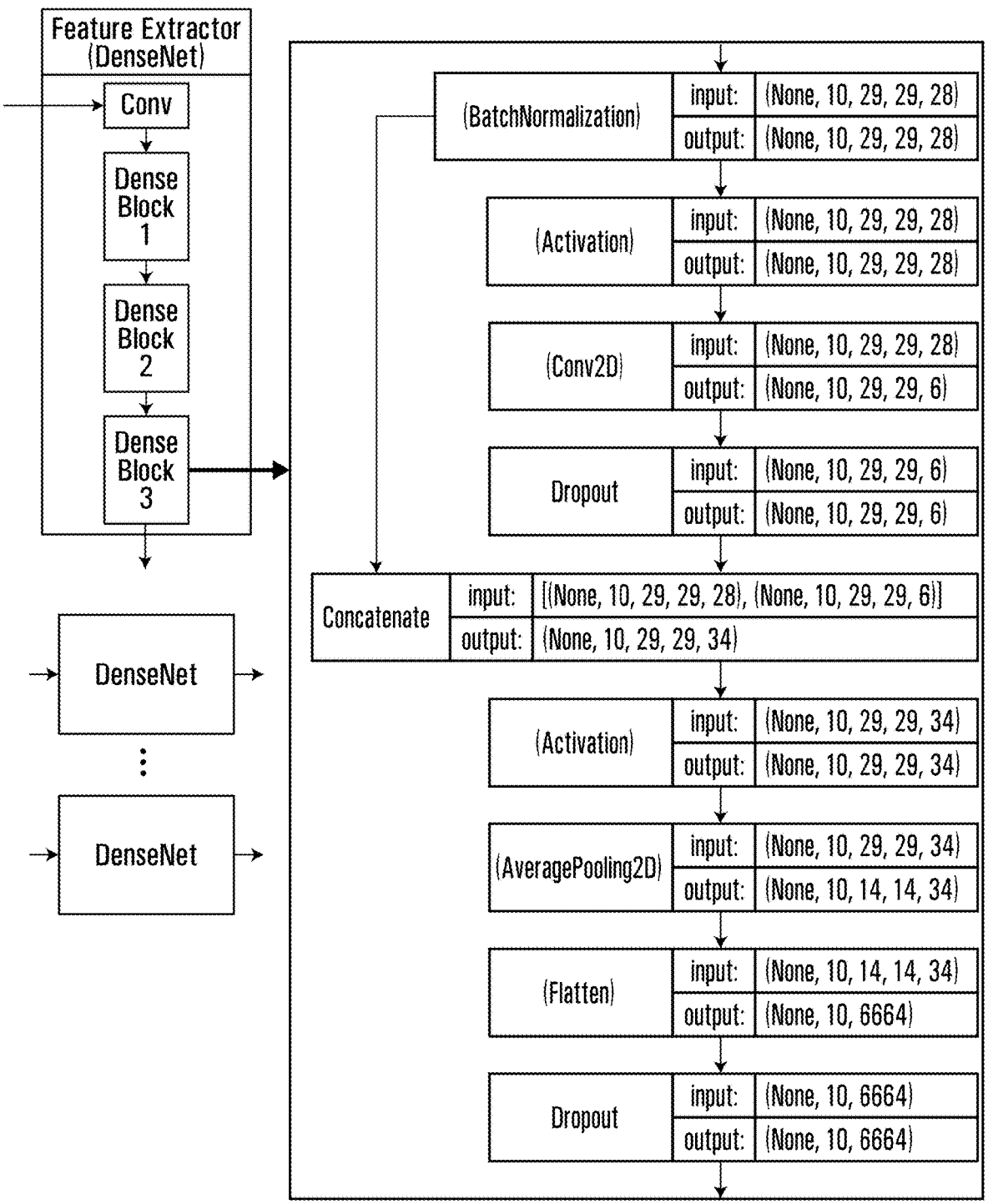
FIG. 7 is a representation of part of the neural network shown in FIG. 4 in accordance with various embodiments of the disclosure.

An exemplary implementation of portions of the commonly defined first feature extracting neural networks including dense blocks 1, 2, and 3 in accordance with various embodiments is shown at 310, 312, and 314 in FIGS. 5, 6, and 7, respectively.

In some embodiments, the commonly defined first feature extracting neural networks (e.g., 304, 306, and 308 shown in FIG. 4) may be each configured to extract features that are encodings of image patterns of a single echo frame which are correlated with the image quality and view category of the single input echo frame. In some embodiments, these features (encodings or mappings) may be in the form of a vector of real-valued numbers (after the flatten operation), and each number may be considered as the level of presence of a specific spatial pattern in the input echo frame. In various embodiments, alternative or additional feature extracting functions and/or neural networks may be used to extract features of the input set of ultrasound images.

In some embodiments, more than one of the commonly defined first feature extracting neural networks may be run concurrently. For example, in some embodiments, block 204 may direct the analyzer processor 100 to run three of the commonly defined first feature extracting neural networks as three identical Convolutional Neural Networks (CNN-1, CNN-2, or CNN-3) in separate threads at the same time in order to prevent lag during particularly long inference times.

In various embodiments, the first feature representations (e.g., as shown at 320, 322, and 324 shown in FIG. 4) output by the commonly defined first feature extracting neural networks 304, 306, and 308 may act as first feature representations of the ultrasound images included in the set of ultrasound images received at block 202. In some embodiments, for example, the first feature representations may each represent a tensor having dimensions 14×14×34 which is flattened to a tensor having length 6664 such that it can be input into a second feature extracting neural network 340.

Block 204 may direct the analyzer processor to store the extracted first feature representations in the location 142 of the storage memory 104, for example, in a feature buffer which may be shared between all three threads. Once all of the ultrasound images included in the set of ultrasound images have been input to an instance of the commonly defined first feature extracting neural network, block 204 may direct the analyzer processor 100 to input the stored first feature representations into a second feature extracting neural network 340 shown in FIG. 4 to generate respective second feature representations, each associated with one of the ultrasound images. In some embodiments, the second feature representations generated by the second feature extracting neural network 340 may act as the one or more extracted feature representations derived by block 204 of the flowchart 200 shown in FIG. 3.

Figure 4:
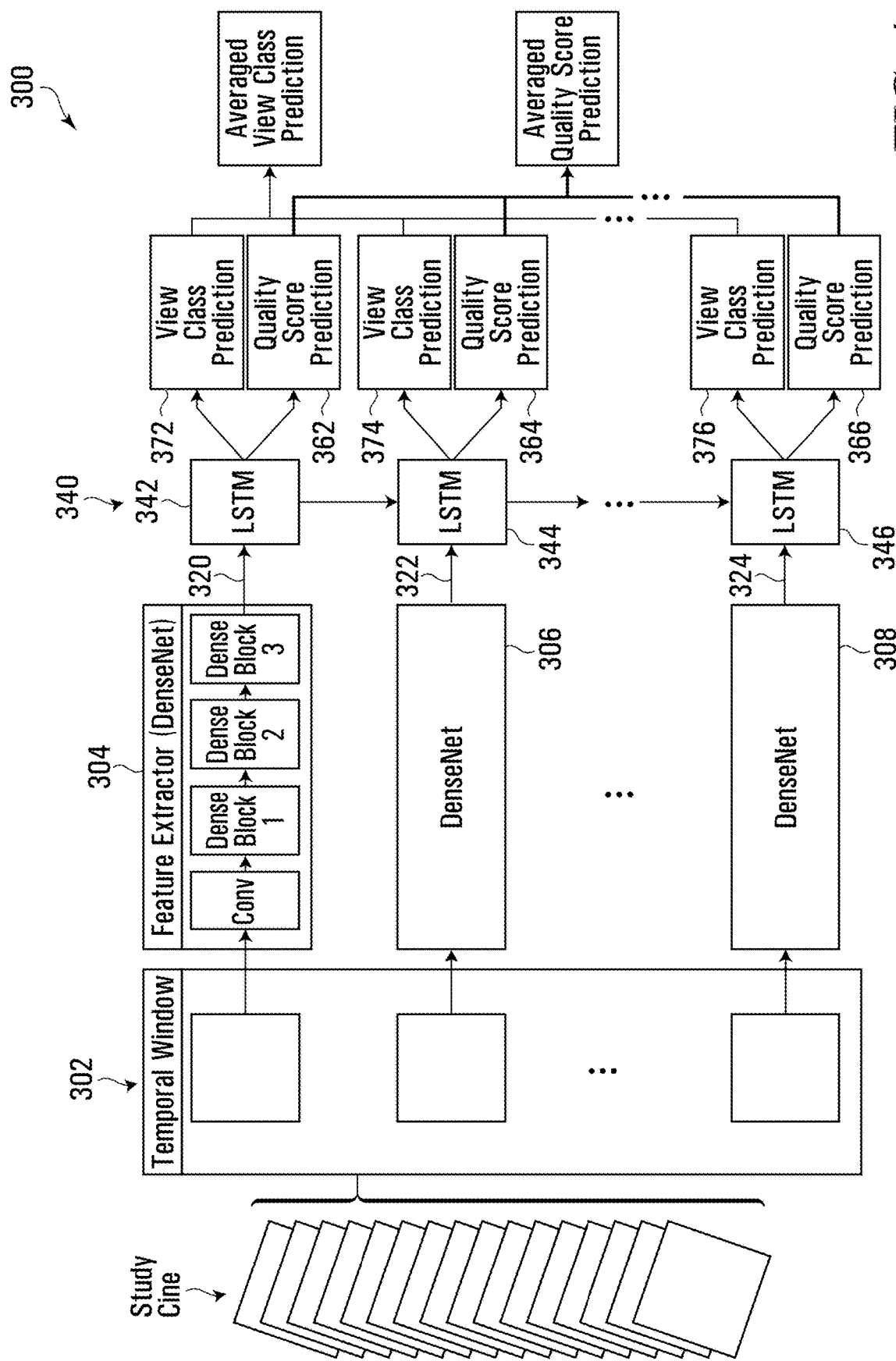
FIG. 4 is a representation of an exemplary neural network that may be used in the system shown in FIG. 1 in accordance with various embodiments of the disclosure.

Referring to FIG. 4, in some embodiments, the second feature extracting neural network 340 may include a plurality of recurrent neural networks (RNNs) (e.g., 342, 344, and 346 shown in FIG. 4). In some embodiments, the RNNs may each be implemented using a long short term memory module (LSTM). In some embodiments parameters defining the second feature extracting neural network 340 may be stored in the location 156 of the storage memory 104 and block 204 may direct the analyzer processor 100 to retrieve the parameters from the location 156 of the storage memory 104. Referring to FIG. 4, each RNN (e.g., 342, 344, and 346 shown in FIG. 4) may output a respective second feature representation, which may be used as an input for further processing. In various embodiments, each of the second feature representations may be a tensor having a length of 128.

In some embodiments, the LSTM layer (which is a type of RNN layer) may operate on the outputs of the Densenet networks of multiple frames. As a result, in some embodiments, the features extracted by the LSTM networks may be encodings of both spatial and temporal patterns of a multitude of echo frames. The sequence of frames whose spatial and temporal patterns contribute to the extracted features may depend on the type of RNN layer included in the second feature extracting neural network 340. In some embodiments, conventional RNN architectures may look backward in time and extract features from the previous N (e.g. N=10) frames. However, in various embodiments, other types of RNNs may be considered/used (i.e. bidirectional RNN) where features may be extracted from the collective of previous and future frames. In various embodiments, the number of frames included in the feature extraction of the RNNs (such as LSTM) could be N=10 or more. In some embodiments, the features may be in the form of real-valued numbers (for example, the features may usually be between −1 and 1 as the activation function of RNN is usually hyperbolic tangent). In some embodiments, each number may be considered as representing a level of presence of a specific spatial and temporal pattern.

In various embodiments, block 204 may direct the analyzer processor 100 to store the second feature representations in the location 144 of the storage memory 104.

Referring to FIG. 3, in various embodiments, blocks 206 and 208 may be executed sequentially or in parallel. Block 206 directs the analyzer processor 100 to determine based on the derived one or more extracted feature representations from block 202, a quality assessment value representing a quality assessment of the set of ultrasound images.

Block 206 may direct the analyzer processor 100 to retrieve the second feature representations from the location 144 of the storage memory 104, the second feature representations acting as the one or more extracted feature representations. Block 206 may direct the analyzer processor 100 to use the second feature representations as inputs to a quality assessment value specific neural network configured to produce as an output a representation of a quality assessment value. In some embodiments, block 206 may direct the analyzer processor 100 to input each of the second feature representations into an implementation of a commonly defined quality assessment value specific neural subnetwork (e.g., 362, 364, and 366) to generate a quality assessment value for each of the input second feature representations. Referring to FIG. 4, in various embodiments the commonly defined quality assessment value specific neural subnetworks may each be defined by the same neural network parameters. In some embodiments, parameters defining the quality assessment value specific neural subnetworks may be stored in the location 158 of the storage memory 104 and block 206 may direct the analyzer processor 100 to retrieve the parameters from the location 158 of the storage memory 104.

Figure 8:
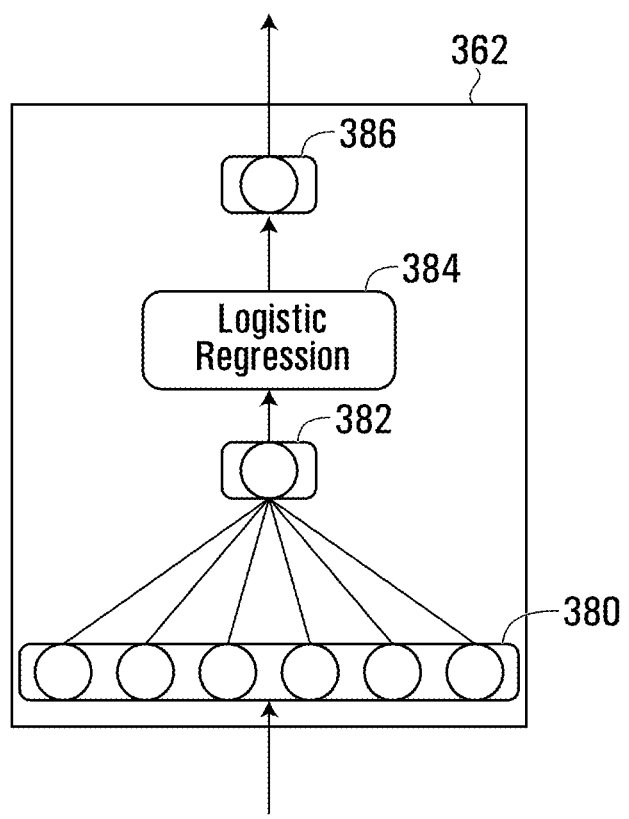
FIG. 8 is a representation of part of the neural network shown in FIG. 4 in accordance with various embodiments of the disclosure.

In various embodiments, each of the commonly defined quality assessment value specific neural subnetworks may apply logistic regression to the input second feature representations to generate a scalar value representing quality of an ultrasound image. Referring to FIG. 8, there is shown a detailed representation of the quality assessment value specific neural subnetwork 362 in accordance with various embodiments. The quality assessment value specific neural subnetwork 362 shown in FIG. 8 is represented in a simplified manner as it may apply to a single cine (i.e., for providing an output having dimension 1). In various embodiments, each of the commonly defined quality assessment value specific neural subnetworks may be defined by the same neural network parameters.

Referring to FIG. 8, in some embodiments, the quality assessment value specific neural subnetwork 362 may include input nodes 380 for holding the output of the second feature extracting neural network 342. In some embodiments, the input nodes 380 may hold a 1×128 feature tensor, for example. In some embodiments, input nodes 364 may be connected to a feature node 382, which may, for example, hold a 1×1 feature tensor acting as an input for a logistic regression function 384. The logistic regression function 384 may be connected to an output node 386, which may include a 1×1 probability tensor holding an output of the quality assessment value specific neural subnetwork 362. In some embodiments, output node 386 may hold a value in the range of [0,1], where a value of 0 corresponds to a bad quality and a value of 1 corresponds to perfect quality.

Block 206 may direct the analyzer processor 100 to determine an average or mean of the quality assessment values output by the quality assessment value specific determining neural subnetworks and to store the average quality assessment value in the location 150 of the storage memory 104.

Referring back to FIG. 3, block 208 directs the analyzer processor 100 to determine, based on the derived one or more extracted feature representations, an image property associated with the set of ultrasound images. In some embodiments, the image property may be a view category. In some embodiments, block 208 may direct the analyzer processor 100 to retrieve the second feature representations from the location 144 of the storage memory 104, the second feature representations acting as the one or more extracted feature representations. Block 208 may direct the analyzer processor 100 to use the second feature representations as inputs to a view category specific neural network configured to produce as an output a representation of a view category. In some embodiments, block 208 may direct the analyzer processor 100 to input each of the second feature representations into an implementation of a commonly defined view category specific neural subnetwork (e.g., 372, 374, and 376) to determine a view category for each of the input second feature representations.

Referring to FIG. 4, in various embodiments the commonly defined view category specific neural subnetworks may each be defined by the same neural network parameters. In some embodiments parameters defining the view category specific neural network may be stored in the location 160 of the storage memory 104 and block 208 may direct the analyzer processor 100 to retrieve the parameters from the location 160 of the storage memory 104.

Figure 9:
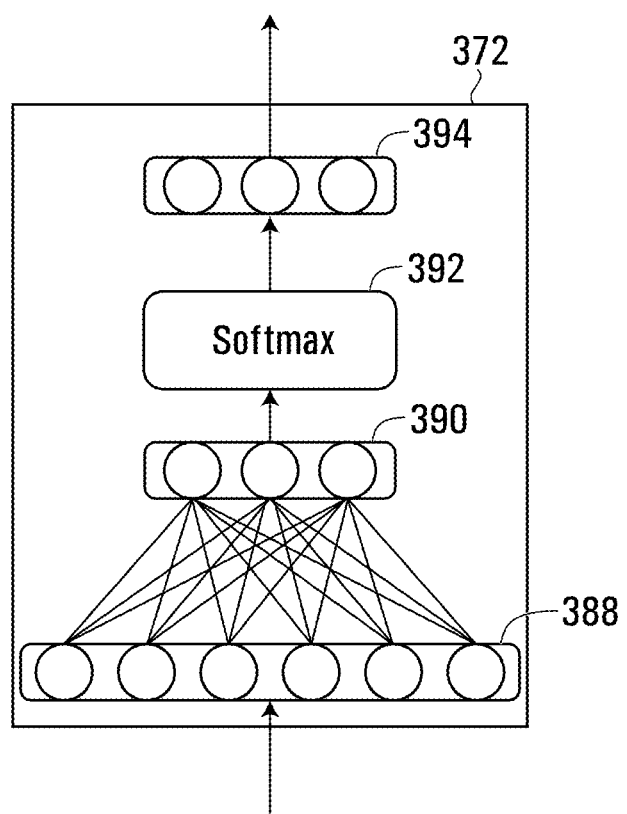
FIG. 9 is a representation of part of the neural network shown in FIG. 4 in accordance with various embodiments of the disclosure.

In various embodiments, each of the commonly defined view category specific neural subnetworks may apply a softmax to the input second feature representations to generate a probability vector wherein each position in the vector corresponds to a view category and the value stored therein represents a probability that the ultrasound image is in the view category corresponding to the vector position. For example, where there are fourteen (14) possible view categories, the output of the view category specific neural subnetwork 372 may be a 14-element length probability vector. In various embodiments, each position in the output probability vector may represent a determined probability that the input set of ultrasound images depicts a particular view category, such as, for example, one chosen from AP2, AP3, AP4, AP5, PLAX, RVIF, PSAXA, PSAXM, PSAXPM, PSAXAP, SC4, SC5, IVC, and SUPRA Referring to FIG. 9, there is shown a detailed representation of the view category specific neural subnetwork 372 in accordance with various embodiments. The view category specific neural subnetwork 372 shown in FIG. 9 is represented in a simplified manner as it may apply to a single cine case (i.e., for providing an output having dimension 1×14). In various embodiments, each of the commonly defined view category specific neural subnetworks may be defined by the same neural network parameters.

Referring to FIG. 9, in some embodiments, view category specific neural subnetwork 372 may include input nodes 388 for holding the output of the second feature extracting neural network 342. In some embodiments, the input nodes 388 may hold a 1×128 feature tensor, for example. In some embodiments, input nodes 388 may be connected to feature nodes 390, which may, for example, hold a 1×14 feature tensor acting as an input for a softmax function 392. The softmax function 392 may be connected to an output node 394, which may include a 1×14 probability tensor holding an output of the view category specific neural subnetwork 372. In some embodiments, output node 394 may hold values that are each in the range of [0,1] and the sum of the values may be equal to 1.

Block 208 may direct the analyzer processor 100 to determine an average of the probability vectors output by the view category specific determining neural subnetworks and to store a representation of the view category associated with the vector position having the highest average probability in the location 152 of the storage memory 104.

Referring back to FIG. 3, block 210 directs the analyzer processor 100 to produce signals representing the quality assessment value and the image property for causing the quality assessment value and the image property to be associated with the set of ultrasound images. In some embodiments, block 210 may direct the analyzer processor 100 to produce signals for causing a representation of the quality assessment value and a representation of the image property to be displayed by the display 18 in association with the set of ultrasound images. For example, in some embodiments, block 210 may direct the analyzer processor 100 to retrieve the quality assessment value from the location 150 of the storage memory 104 and to retrieve the view category from the location 152 of the storage memory 104 and to transmit signals to the display 18 via the interface 130 of the I/O interface 112 shown in FIG. 2, representing the quality assessment value and the view category for causing the graphical user interface 400 shown in FIG. 10 to be displayed by the display 18.

Figure 10:
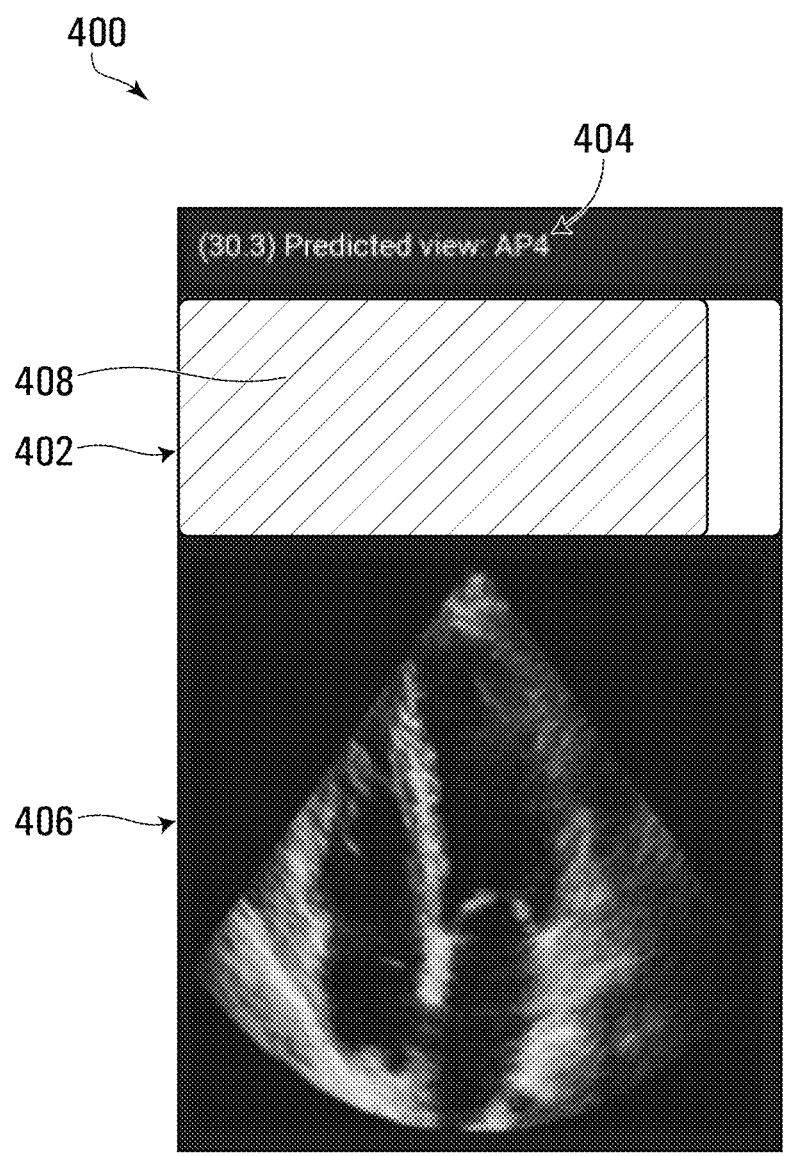
FIG. 10 is a representation of a display that may be provided by the system shown in FIG. 1 in accordance with various embodiments of the disclosure.

Referring to FIG. 10, the graphical user interface 400 includes a bar indicator 402 showing a graphical representation of the quality assessment value and an indicator 404 representing the view category in association with a representation of an ultrasound image 406 included in the set of ultrasound images. In various embodiments, the bar indicator 402 may include a fill portion 408 which grows in length as the quality assessment value increases. In some embodiments, the fill portion 408 may change color depending on the quality assessment value. In various embodiments, an operator viewing the displayed representations of both the quality assessment value and the view category, may be able to use this information to recognize the specific features and structures required of various views and/or to capture diagnostically relevant heart cines.

In various embodiments, the flowchart 200 shown in FIG. 3 may be executed repeatedly and/or continuously to update the quality assessment value bar indicator 402 and view category indicator 404 of the graphical user interface 400 shown in FIG. 10.

Neural Network Training

As discussed above, in various embodiments, the analyzer 14 may use a neural network 300 shown in FIG. 4 which includes various subnetworks. In various embodiments, the parameters defining the neural network 300 may be stored in the storage memory 104 and may have been previously determined during neural network training. For example, in some embodiments, the system 10 shown in FIG. 1 may include a neural network trainer configured to train the neural network 300.

Figure 11:
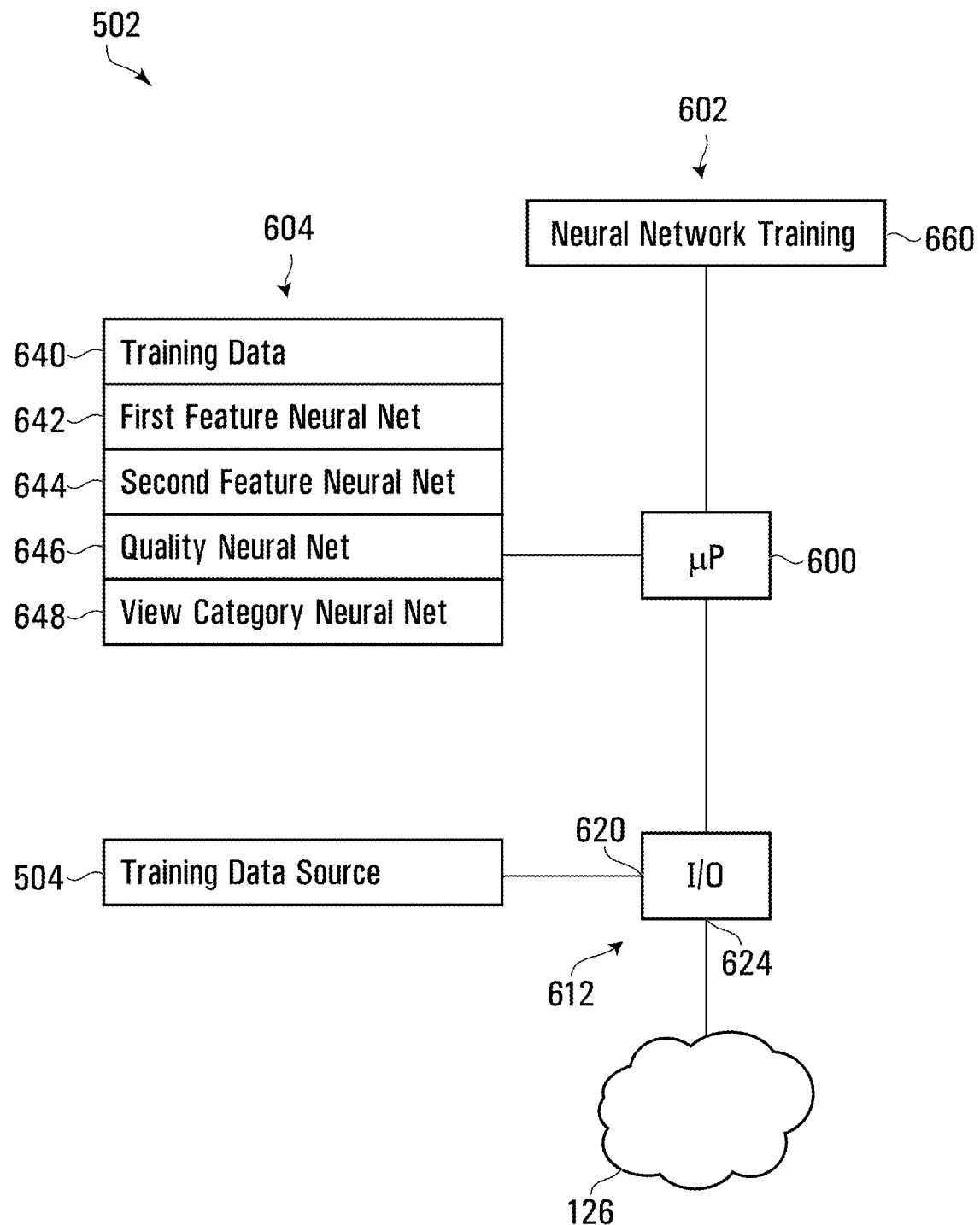
FIG. 11 is a schematic view of a neural network trainer that may be included in the system shown in FIG. 1 in accordance with various embodiments of the disclosure.

Referring to FIG. 11, a schematic view of a neural network trainer 502 which may be included in the system 10 shown in FIG. 1 in various embodiments is shown. In various embodiments, the neural network trainer 502 may be incorporated in one or more computers, for example.

Referring to FIG. 11, in various embodiments, the neural network trainer 502 includes a processor circuit including a trainer processor 600 and a program memory 602, a storage memory 604, and an I/O interface 612, all of which are in communication with the trainer processor 600.

The I/O interface 612 includes an interface 620 for communicating with a training data source 504. In some embodiments, the interface 620 may provide a connection to a network to which the training data source 504 is connected such that communication between the training data source 504 and the trainer 502 is facilitated. For example, in some embodiments, the training data source 504 may include a server computer for storing and archiving medical electronic images and associated image properties, such as, for example, an archive device. In some embodiments, the I/O interface 612 also includes an interface 624 for facilitating networked communication with the analyzer 14 through the network 126. In some embodiments, the interface 620 may provide a connection to the network 126 and the training data source 504 may also be connected to the network 126.

Processor-executable program codes for directing the trainer processor 600 to carry out various functions are stored in the program memory 602. The program memory 602 includes a block of codes 660 for directing the neural network trainer 502 to perform neural network training functions.

The storage memory 604 includes a plurality of storage locations including location 640 for storing training data, location 642 for storing first feature extracting neural network data, location 644 for storing second feature extracting neural network parameter data, location 646 for storing quality assessment value specific neural network parameter data, and location 648 for storing view category specific neural network parameter data.

In various embodiments, the neural network trainer 502 may be configured to train the neural network 300 shown in FIG. 4 based on a plurality of sets of ultrasound images, each set associated with a quality assessment value and an image property, such as a view category.

Figure 12:
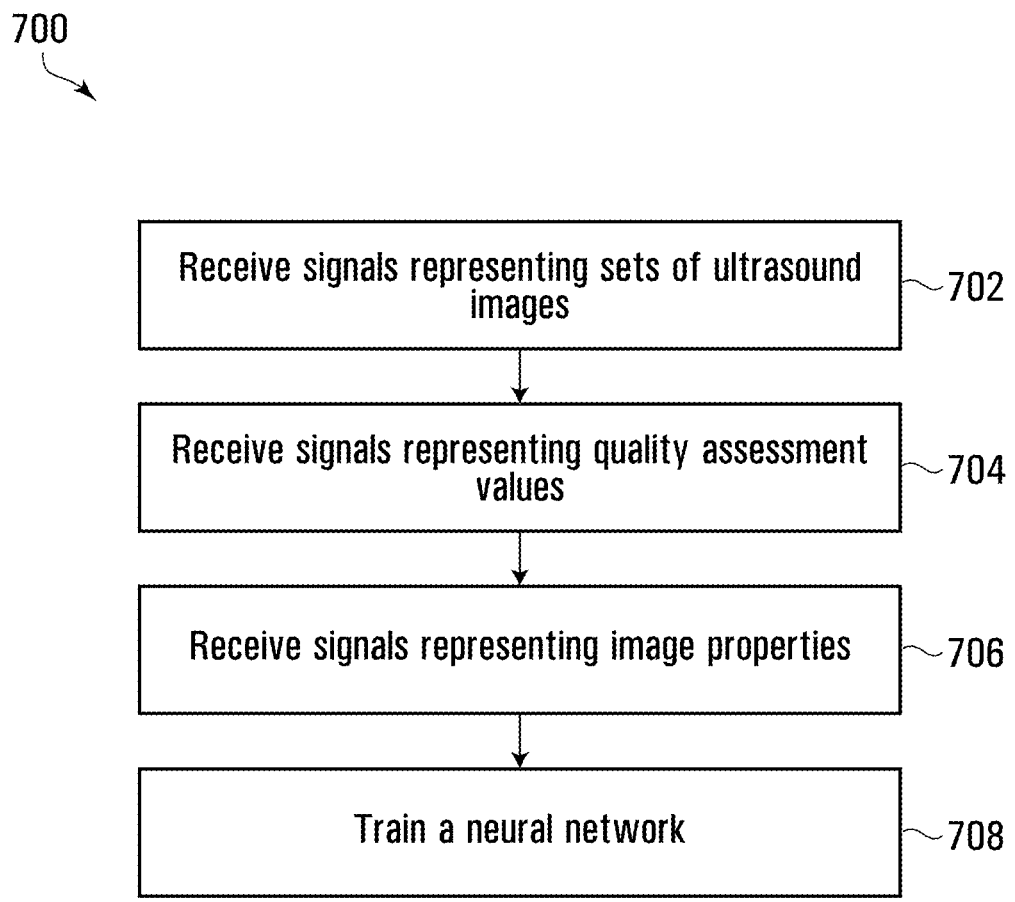
FIG. 12 is a flowchart depicting blocks of code for directing the trainer shown in FIG. 11 to perform neural network training functions in accordance with various embodiments of the disclosure.

Referring now to FIG. 12, a flowchart depicting blocks of code for directing the trainer processor 600 shown in FIG. 11 to perform neural network training to facilitate ultrasonic image analysis functions in accordance with various embodiments is shown generally at 700. The blocks of code included in the flowchart 700 may be encoded in the block of codes 660 of the program memory 602 shown in FIG. 11 for example.

Referring to FIG. 12, the flowchart 700 begins with block 702 which directs the trainer processor 600 shown in FIG. 11 to receive signals representing a plurality of sets of ultrasound training images. In various embodiments, block 702 may direct the trainer processor 600 to receive the signals representing the plurality of sets of ultrasound training images from the training data source 504 via the interface 620 of the I/O interface 612 shown in FIG. 11. In various embodiments, block 702 may direct the trainer processor 600 to store the sets of ultrasound training images in the location 640 of the storage memory 604 of the trainer 502 shown in FIG. 11.

In some embodiments, each set of ultrasound images may be a temporally ordered set of ultrasound images representing a video or cine of a respective subject. In some embodiments, each subject may be a heart of a patient and each set of ultrasound images may be referred as an echocine.

Block 704 then directs the trainer processor 600 to receive signals representing quality assessment values, each of the quality assessment values associated with one of the sets of ultrasound training images and representing a quality assessment of the associated set of ultrasound training images. In some embodiments, block 704 may direct the trainer processor 600 to receive the signals representing the quality assessment values from the training data source 504 via the interface 620 of the I/O interface 612 shown in FIG. 11. In various embodiments, the quality assessment values may have been previously provided to the training data source 504. For example, in some embodiments, the quality assessment values may have been previously provided by an expert who has been trained to determine quality of the sets of ultrasound images. For example, in some embodiments, the quality assessment values may be values between 0% and 100% representing whether the set of ultrasound images are suitable for subsequent quantified clinical measurement of anatomical features and/or to assist in diagnosing a medical condition.

Block 704 may direct the trainer processor 600 to store the received quality assessment values in the location 640 of the storage memory 604. For example, in some embodiments, block 704 may direct the trainer processor 600 to store each of the quality assessment values in association with the set of ultrasound images to which they apply.

Block 706 then directs the trainer processor 600 to receive signals representing image properties, each of the image properties associated with one of the sets of ultrasound training images. In some embodiments, the image properties may each be a view category. In some embodiments, block 706 may direct the trainer processor 600 to receive signals representing view categories from the training data source 504 via the interface 620 of the I/O interface 612 shown in FIG. 11. In various embodiments, the view categories may have been previously provided to the training data source 504. For example, in some embodiments, the view categories may have been previously provided by an expert who has been trained to determine view categories for the sets of ultrasound images. For example, in some embodiments, the subject imaged in the sets of ultrasound images may be a heart and the view categories may be chosen from the following views: AP2, AP3, AP4, AP5, PLAX, RVIF, PSAXA, PSAXM, PSAXPM, PSAXAP, SC4, SC5, IVC, and SUPRA.

Block 706 may direct the trainer processor 600 to store the received view categories in the location 640 of the storage memory 604. For example, in some embodiments, block 706 may direct the trainer processor 600 to store each of the view categories in association with the set of ultrasound images to which they apply.

In various embodiments, the training data source 504 may send the sets of ultrasound images in association with the quality assessment values and the image properties and so blocks 702, 704, and 706 may be executed concurrently.

Block 708 then directs the trainer processor 600 to train a neural network, the training involving, for each set of the plurality of sets of ultrasound training images, using the set of ultrasound training images as an input to the neural network and using the quality assessment values and the image properties associated with the set of ultrasound training images as desired outputs of the neural network. For example, in some embodiments, the neural network trained at block 708 may be the neural network 300 shown in FIG. 4.

Accordingly, block 708 may direct the trainer processor 600 to train the neural network 300 shown in FIG. 4 using each of the sets of ultrasound images stored in the location 640 of the storage memory 604 as inputs and using each of the associated quality assessment values and view categories stored in the location 640 of the storage memory 604 as desired outputs when the associated set of ultrasound images are used as inputs.

In some embodiments, block 708 may direct the trainer processor 600 to train the neural network 300 shown in FIG. 4 using batches. For example, in some embodiments, block 708 may direct the trainer processor 600 to randomly select 32 sets of ultrasound images or cine clips from the location 640 of the storage memory 604, and block 708 may direct the trainer processor 600 to choose 10 consecutive ultrasound images or frames from each set to make a batch such that the batch is filed with 320 frames of images with a dimension or size of 120×120×1 (in various embodiments, the ultrasound image data may be grayscale and therefore the last channel may have 1 dimension). This batch may be considered an input tensor, with the tensor size is 32×10×120×120×1. In various embodiments, the first dimension 32 may be called the batch size. In some embodiments, a large batch size may help with parallelizing the computation. In some embodiments, batch size may be any number as long as the memory permits and, in some embodiments, 32 may be chosen as the batch size for training.

Block 708 may direct the analyzer processor 100 to feed the input tensor to the neural network 300, where each ultrasound image first goes through an instance of the commonly defined first feature extracting neural network or DenseNet feature extraction module. The output tensor of the commonly defined first feature extracting neural networks or DenseNet modules may be 32×10×A×B×C, where "A×B×C" denotes the dimensionality of the output feature for each frame. In some embodiments, the output tensor may be of dimension 32×10×14×14×34, for example.

Block 708 then directs the trainer processor 600 to flatten the output tensor into 32×10×(A*B*C), or 32×10×6664 in some embodiments, for example, so that the second feature extracting neural network 340 (e.g., the LSTM module, in some embodiments) can process it. After the second feature extracting neural network 340 processes the 32×10×(A*B*C) feature tensor, it may produce a 32×10×128 feature tensor, and block 708 may direct the trainer processor 600 to use the 32×10×128 feature tensor as inputs for both the quality assessment value specific neural network and view category specific neural network.

Block 708 may direct the trainer processor 600 to compare the predictions made within the quality assessment value specific neural network and view category specific neural network with the respective ground truths, or desired outputs. In various embodiments, the predictions may be compared to the quality assessment values and view categories stored in the location 640 of the storage memory 604. An initial output of the view category specific neural network may be of dimension 32×10×14 (classes) and block 708 may direct the trainer processor 600 to determine a mean over the 10 frames for the initial output to generate a tensor of dimension 32×14. An initial output of the quality assessment value specific neural network may be of dimension 32×10×1 and block 708 may direct the trainer processor 600 to determine a mean over the 10 frames for the initial output to generate a tensor of dimension 32×1.

Block 708 may direct the trainer processor 600 to determine a difference between the view classification predictions (32×14) and the ground truth (as previously provided by an expert, for example), as measured by the cross-entropy loss function, which produces scalar values, i.e. 32×14→32×1. In various embodiments, block 708 may direct the trainer processor 600 to average the 32×1 values into 1 scalar value representing how well the predictions match the ground truth labels. Similarly, for the quality estimation, the difference may be measured by the binary cross-entropy loss function, which is the cross-entropy loss function working on two classes (i.e., bad quality:0, excellent quality:1). This also produces a scalar value, i.e., 32×1→1 representing how well the predictions match the ground truth labels. In various embodiments, a low scalar value representing how well the predictions match the ground truth labels may mean better matching. In various embodiments, the differences may also or alternatively be measured by other types of loss functions such as, for example, an absolute difference loss function or a squared difference loss function.

Block 708 may direct the trainer processor 600 to add these two loss values together and to train the network based on these summed losses. Block 708 may direct the trainer processor 600 to use a back-propagation method, wherein block 708 directs the trainer processor 600 to compute the gradient with respect to the neural network or model parameters (i.e., the weights and bias in every layer) and the gradient is used to update the neural network or model parameters. In various embodiments, the updated parameters may be stored in the locations 642, 644, 646, and 648 of the storage memory 604.

In various embodiments the flowchart 700 may be executed many times in order to train the neural network 300 shown in FIG. 4 adequately. For example, in some embodiments, the plurality of sets of ultrasound training images may include 13400 sets or echo cine clips, and the trainer 502 may be configured to run 100 epochs where each epoch runs through the entire training with batch size 32.

Accordingly, in some embodiments, the flowchart 700 may be executed 13400/32=419 times per epoch and 41900 times in total over all of the epochs.

In various embodiments, by adding the loss values together to train the network based on these summed losses, the neural network 300 may be trained more quickly and may provide more accurate results than a neural network which is trained based on loss values provided only by looking at desired quality assessment values or based on loss values provided only by looking at desired view categories. In some embodiments, this may also or alternatively result in a compact neural network that may consume less memory and/or use less battery power for computation.

In some embodiments, the flowchart 700 may include a block for directing the trainer processor 600 to produce signals representing the trained neural network for causing the neural network to be used to predict a quality assessment value and a view category based on an input set of ultrasound images. For example, in some embodiments, a block of codes may direct the trainer processor 600 to transmit the neural network parameter information stored in the locations 642, 644, 646, and 648 of the storage memory 604, which defines the neural network 300 to the analyzer 14 via the interface 624 and the network 126.

A block of codes included in the block 170 of the program memory 102 of the analyzer 14 shown in FIG. 2 may direct the analyzer processor 100 to receive the neural network parameter information via the interface 124 of the I/O interface 112 and to store the neural network parameter information in the locations 154, 156, 158, and 160 of the storage memory 104.

Highest Quality Assessment Value

Referring to FIG. 3, in some embodiments, flowchart 200 may include a block of codes for directing the analyzer processor 100 to store an ultrasound image associated with the highest quality assessment value for each view category.

In various embodiments the block may direct the analyzer processor 100 to, for each view category, update/replace an ultrasound image stored in the location 162 of the storage memory 104 such that the ultrasound image stored is an ultrasound image that is associated with the highest quality assessment value, for that view category.

In some embodiments, the block may be executed after blocks 206 and 208 of the flowchart 200 have been executed. Upon analysis of a first set of ultrasound images for a given view category, the block may direct the analyzer processor 100 to, after determining a quality assessment value for each of the ultrasound images included in the first set of ultrasound images and determining a view category for the set of ultrasound images, identify the ultrasound image associated with the highest determined quality assessment value and store the ultrasound image in association with the determined quality assessment value and the determined view category in the location 162 of the storage memory 104.

Upon analysis of subsequent sets of ultrasound images for the view category, The block may direct the analyzer processor 100 to, for each determined quality assessment value, determine whether the quality assessment value is higher than the quality assessment value stored in association with the ultrasound image and the same view category in the location 162 of the storage memory 104. The block may direct the analyzer processor 100 to, if the determined quality assessment value is higher than the stored quality assessment value, store the ultrasound image associated with the determined quality assessment in the location 162 of the storage memory 104 in association with the determined quality assessment value and the determined view category. In some embodiments, the block may direct the analyzer processor 100 to replace any previously stored quality assessment value and ultrasound image stored in the location 162 of the storage memory 104 in association with the determined view category with the determined quality assessment value and the associated ultrasound image. In various embodiments, this may facilitate storage of ultrasound images associated with the highest determined quality assessment values, for each view category, in the location 162 of the storage memory 104.

In various embodiments, an operator may not even know this is happening, but when it comes to review the high-quality cines afterwards, it may be a very useful tool to find the best quality images for each cine. In various embodiments, an operator may initiate a block of codes included in the program memory 102 for directing the analyzer processor 100 to later retrieve the ultrasound images stored in the location 162 of the storage memory and to produce signals representing the ultrasound images for causing the ultrasound images to be displayed by the display 18. In various embodiments, in this way, the operator may easily view the best quality images for each view category.

Various Embodiments

In some embodiments, a system generally similar to the system 10 shown in FIG. 1 and discussed herein may use a neural network having additional and/or alternative architecture to the architecture of the neural network 300 shown in FIG. 4 and discussed herein.

In some embodiments, the functionality provided by the quality assessment value specific neural network and the image property specific neural network may be implemented using a combined neural network configured to output both a quality assessment value and a representation of the image property.

While various embodiments have been described herein wherein the image property used in the system 10 is a view category, in some embodiments, the system 10 may use another image property. In such embodiments, the analyzer 14 may be configured to apply a neural network that outputs a quality assessment value and the other image property. Further, in such embodiments, the trainer 502 may be configured to train a neural network that outputs a quality assessment value and the other image property. For example, in some embodiments, the image property may include a representation of any or all of the elements included in the following list, for example:

Cardiac
    Left ventricular ejection fraction (LVEF)
    Left atrial ejection fraction (LAEF)
    Strain, both local and global
    Pericardial Effusion
    Heart rate
    Cardiac phase
FAST (Emergency Medicine)
    Free Fluid
Inferior vena cava (IVC)
Volume Assessment
Obstetrics
    Ovarian torsion
    Endometritis
    Detection of fetal pole Calculation of gestational age
Gallbladder
  Gallstones
Pulmonary
  Pneumothorax
  Pleural Effusion
  Pneumonia/Consolidation
Ocular
  Retinal Detachment
  Vitreous Hemorrhage
Musculoskeletal
  Joint Effusion
  Tendon Rupture
  Fracture Identification
Renal
  Hydronephrosis
  Nephrolithiasis
Deep vein thrombosis (DVT)
Aorta
Intrauterine pregnancy
  Intrauterine Pregnancy
  Fetal Heart Rate
Soft Tissue
  Cellulitis
  Abscess
  Foreign body
Scrotal
  Testicular Torsion
  Hydrocele
  Epididymitis In various embodiments, the system 10 shown in FIG. 1 may be used to facilitate analysis of ultrasound images in various subjects. For example, in some embodiments, various tissues/organs may be analyzed using an embodiment of the system 10. For example, in some embodiments, the system 10 may be used for liver analysis, spine analysis, fat tissue analysis and other tissue/organ analysis etc. For example, in some embodiments, the system 10 may be used for analysis of any or all of the elements in the above list. In various embodiments, procedures for which the system 10 may be used may include, for example:

Heart valve repair using transesophageal echocardiography
  Nerve blocks
  Vascular access
  Arthrocentesis
  Lumbar puncture
  Paracentesis
  Thoracentesis
  Airway In various embodiments, a system generally similar to the system 10 shown in FIG. 1 may include an analyzer that performs the functionality of the analyzer 14 described herein but that takes a different form. For example, in various embodiments, the analyzer may not be implemented using a mobile device. In some embodiments the analyzer may be implemented within an ultrasound machine, for example. In such embodiments, the ultrasound monitor may provide some of the functionality described herein as provided by the display 18 and/or ultrasound image data may not need to be transferred off of the ultrasound machine.

In various embodiments, the ultrasound machine 16 may take additional or alternative forms to the schematic representation shown in FIG. 1. For example, in some embodiments, the ultrasound machine 16 may be implemented wherein the ultrasound machine and the transducer are one unit and the ultrasound machine produces wireless signals for causing a display to display the ultrasound images. For example, in some embodiments, the ultrasound machine may wirelessly transmit ultrasound data to a mobile device or phone for display. In some embodiments, the mobile device or phone displaying the ultrasound images may act as the analyzer 14 or transmit the ultrasound data to a secondary mobile device acting as the analyzer 14, for analysis.

In various embodiments the set of ultrasound images analyzed in the system 10 described herein may be a single ultrasound image.

In some embodiments, the trainer may include a user interface and block 704 may direct the trainer processor 600 to receive the quality assessment values and/or the view category information via the user interface from an expert interacting with the user interface.

In various embodiments, the analyzer 14 may be implemented using an Android mobile device running a customized mobile implementation of the TensorFlow inference engine. In some embodiments, by multi-threading four TensorFlow instances together, the analyzer 14 may be able to execute the flowchart 200 shown in FIG. 3 for analyzing images being received at 30 Hz with a latency of under 0.4 seconds.

In various embodiments, while three threads are running the first feature extracting neural networks for a set of ultrasound images, a fourth thread may run the rest of the neural network 300 shown in FIG. 4 for a previous set of ultrasound images for which the feature representations were already determined. For example, FIG. 13 shows a timing diagram 750 of how the threads 752, 754, 756, and 758 may be run concurrently according to various embodiments.

Figure 13:
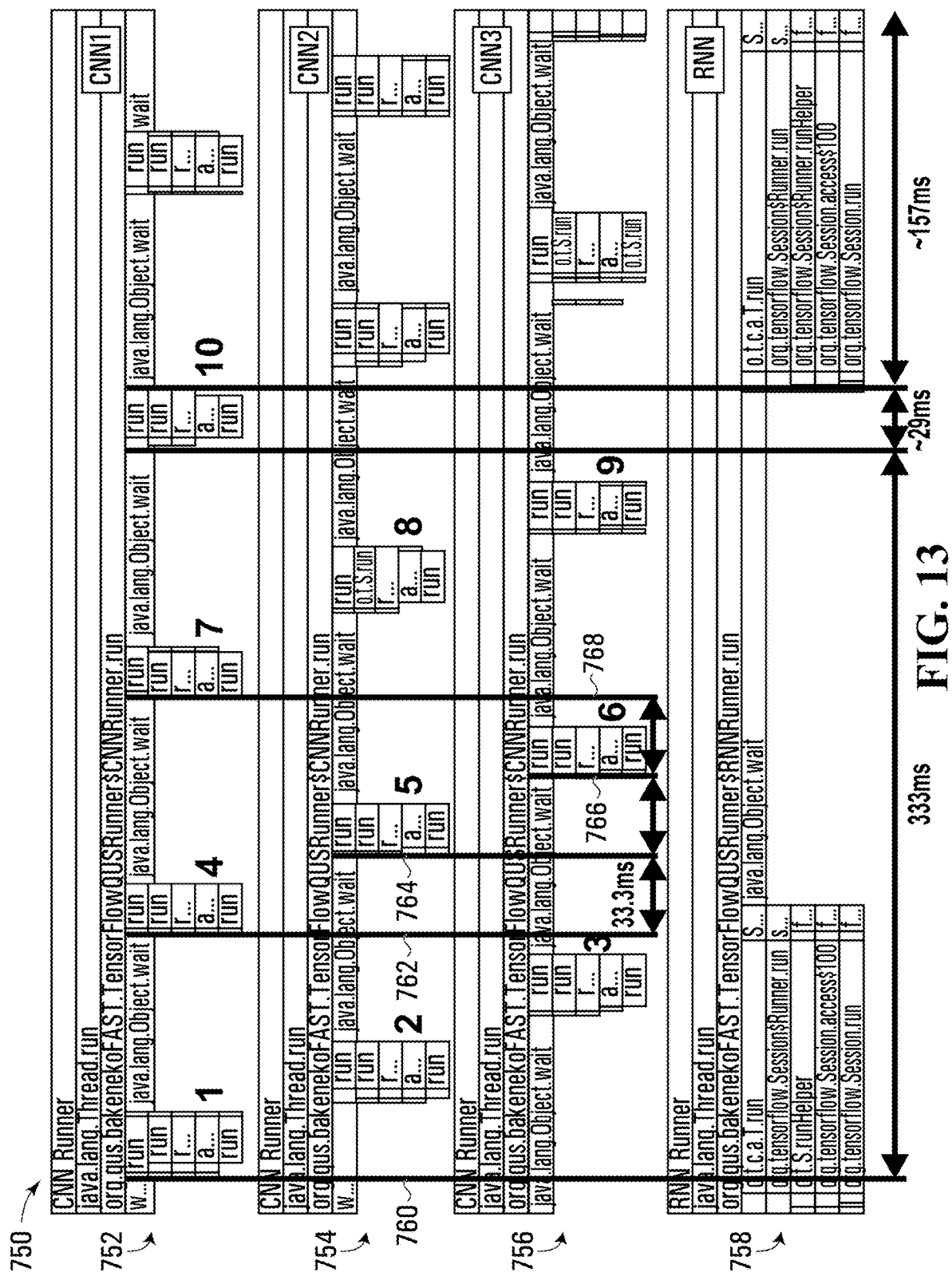
FIG. 13 is a timing diagram representing thread timing that may be used in the system shown in FIG. 1 in accordance with various embodiments of the disclosure.

Referring to FIG. 13, three first feature extracting neural network or CNN threads can be seen extracting features from ten consecutive input frames before waking a waiting RNN thread configured to run the rest of the neural network 300 shown in FIG. 4, which then runs the LSTMs, quality assessment value and view category prediction on the buffered features extracted by the CNN threads. The target frame rate for the system may be set at 30 Hz, which can be inferred by the lines 760, 762, 764, 766, and 768 representing the arrival of input frames. In some embodiments, the mean run-time for the first feature extracting neural networks (including feeding the input, running the network, and fetching the output) may be 28.76 ms with a standard deviation of 16.42 ms and the mean run time of the rest of the neural network 300 may be 157.48 ms with a standard deviation of 21.85 ms. Therefore, the mean latency of the feedback may be 352.58 plus or minus 38.27 ms, when measured from the middle of the ten-frame sequence.

In various embodiments, in order to prevent lag resulting from the build-up of unprocessed frames, the first feature extracting neural network threads and RNN need to finish running before they are requested to process the next batch of data. In some embodiments, to accomplish this reliably, all the per-frame processing must complete within $T_{max, first\ feature}$, calculated as follows:

$$T_{max, first\ feature} = (\# \text{ of first feature threads}) * 1/FPS = 3/30 = 100 \text{ ms}$$

while the rest of the neural network 300 may need to complete its processing before the features from the next ten frames are extracted:

$$T_{max, RNN} = (\text{buffer length}) * 1/FPS = 10/30 = 333.33 \text{ ms}$$

With the chosen three first feature extracting neural network threads and one thread for the rest of the neural network 300 configuration, in various embodiments, the application may require few threads while still providing enough tolerance to avoid frame build-up.

In various embodiments, neural networks described herein, including the first feature extracting neural networks shown in FIG. 4, for example, may be implemented by using Keras (https://keras.io/), a high-level neural networks API on top of the Tensorflow (https://www.tensorflow.org/) deep learning library backend in Python. The Keras library may be imported as tf.keras from Tensorflow (i.e., tf).

For the components included in the first feature extracting neural networks, in various embodiments, the convolution operation may be implemented by using the function tf.keras.layers.Conv2D, the batch normalization operation may be implemented by using the function tf.keras.layers.BatchNormalization, the ReLU activation operation may be implemented by using the function tf.keras.layers.ReLU, the dropout operation may be implemented by using the function tf.keras.layers.Dropout, the concatenation operation may be implemented by using the function tf.keras.layers.concatenate, and the average pooling operation may be implemented by using the function tf.keras.layers.AveragePooling2D. In various embodiments, for the second feature extracting neural network 340 shown in FIG. 4, the LSTM operation may be implemented by using the function tf.keras.layers.LSTM.

While specific embodiments of the disclosure have been described and illustrated, such embodiments should be considered illustrative of the disclosure only and not as limiting the disclosure as construed in accordance with the accompanying claims.

The invention claimed is:

1. A computer-implemented method of facilitating ultrasonic image analysis of a subject, the method comprising:
receiving signals representing a set of ultrasound images of the subject;
deriving one or more extracted feature representations from the set of ultrasound images;
determining, based on the derived one or more extracted feature representations, a quality assessment value representing a quality assessment of the set of ultrasound images;
determining, based on the derived one or more extracted feature representations, an image property associated with the set of ultrasound images; and
producing signals representing the quality assessment value and the image property for causing the quality assessment value and the image property to be associated with the set of ultrasound images.

2. The method of claim 1 wherein the image property is a view category.

3. The method of claim 2 wherein deriving the one or more extracted feature representations from the ultrasound images comprises, for each of the ultrasound images, deriving a first feature representation associated with the ultrasound image.

4. The method of claim 3 wherein deriving the one or more extracted feature representations comprises, for each of the ultrasound images, inputting the ultrasound image into a commonly defined first feature extracting neural subnetwork to generate the first feature representation associated with the ultrasound image.

5. The method of claim 4 wherein deriving the one or more extracted feature representations comprises concurrently inputting each of a plurality of the ultrasound images into a respective implementation of the commonly defined first feature extracting neural network.

6. The method of claim 4 wherein the commonly defined first feature extracting neural network includes a convolutional neural network.

7. The method of claim 4 wherein deriving the one or more extracted feature representations comprises inputting the first feature representations into a second feature extracting neural network to generate respective second feature representations, each associated with one of the ultrasound images and wherein the one or more extracted feature representations include the second feature representations.

8. The method of claim 7 wherein the second feature extracting neural network is a recurrent neural network.

9. The method of claim 2 wherein determining the quality assessment value comprises inputting the one or more extracted feature representations into a quality assessment value specific neural network and wherein determining the image property comprises inputting the one or more extracted feature representations into an image property specific neural network.

10. The method of claim 9 wherein inputting the one or more extracted feature representations into the quality assessment value specific neural network comprises inputting each of the one or more extracted feature representations into an implementation of a commonly defined quality assessment value specific neural subnetwork and wherein inputting the one or more extracted feature representations into the image property determining neural network comprises inputting each of the one or more extracted feature representations into an implementation of a commonly defined image property specific neural network.

11. The method of claim 2 wherein producing signals representing the quality assessment value and the image property for causing the quality assessment value and the image property to be associated with the set of ultrasound images comprises producing signals for causing a representation of the quality assessment value and a representation of the image property to be displayed by at least one display in association with the set of ultrasound images.

12. A computer-implemented method of training one or more neural networks to facilitate ultrasonic image analysis, the method comprising:
receiving signals representing a plurality of sets of ultrasound training images;
receiving signals representing quality assessment values, each of the quality assessment values associated with one of the sets of ultrasound training images and representing a quality assessment of the associated set of ultrasound training images;
receiving signals representing image properties, each of the image properties associated with one of the sets of ultrasound training images; and
training a neural network, the training comprising, for each set of the plurality of sets of ultrasound training images, using the set of ultrasound training images as an input to the neural network and using the quality assessment values and the image properties associated with the set of ultrasound training images as desired outputs of the neural network.

13. The method of claim 12 wherein each of the image properties is a view category.

14. The method of claim 13 wherein the neural network includes a feature extracting neural network, an image property specific neural network, and a quality assessment value specific neural network and wherein:
the feature extracting neural network is configured to take an input set of the plurality of sets of ultrasound training images as an input and to output one or more extracted feature representations;

the image property specific neural network is configured to take the one or more extracted feature representations as an input and to output a representation of an image property associated with the input set of ultrasound training images; and the quality assessment specific neural network is configured to take the one or more extracted feature representations as an input and to output a quality assessment value associated with the input set of ultrasound training images.

15. The method of claim 14 wherein the feature extracting neural network is configured to, for each of the ultrasound training images included in the input set of ultrasound training images, derive a first feature representation associated with the ultrasound image.

16. The method of claim 15 wherein the feature extracting neural network includes, for each of the ultrasound images included in the input set of ultrasound training images, a commonly defined first feature extracting neural network configured to take as an input the ultrasound training image and to output a respective one of the first feature representations.

17. The method of claim 16 wherein more than one implementation of the commonly defined first feature extracting neural networks are configured to concurrently generate the first feature representations.

18. The method of claim 16 wherein the commonly defined first feature extracting neural network is a convolutional neural network.

19. The method of claim 16 wherein the feature extracting neural network includes a second feature extracting neural network configured to take as an input the first feature representations and to output respective second feature representations, each associated with one of the ultrasound images included in the input set of ultrasound training images and wherein the one or more extracted feature representations include the second feature representations.

20. The method of claim 19 wherein the second feature extracting neural network is a recurrent neural network.

21. A system for facilitating ultrasonic image analysis comprising at least one processor configured to:
receive signals representing a set of ultrasound images of the subject;
derive one or more extracted feature representations from the set of ultrasound images;
determine, based on the derived one or more extracted feature representations, a quality assessment value representing a quality assessment of the set of ultrasound images;
determine, based on the derived one or more extracted feature representations, an image property associated with the set of ultrasound images; and
produce signals representing the quality assessment value and the image property for causing the quality assessment value and the image property to be associated with the set of ultrasound images.

22. The system of claim 21 wherein the image property is a view category.

23. The system of claim 22 wherein the at least one processor is configured to, for each of the ultrasound images, input the ultrasound image into a commonly defined first feature extracting neural subnetwork to generate a first feature representation associated with the ultrasound image.

24. The system of claim 23 wherein the at least one processor is configured to, for each of the ultrasound images, input the ultrasound image into a commonly defined first feature extracting neural subnetwork to generate the first feature representation associated with the ultrasound image.

25. The system of claim 24 wherein the at least one processor is configured to concurrently input each of a plurality of the ultrasound images into a respective implementation of the commonly defined first feature extracting neural network.

26. The system of claim 24 wherein the at least one processor is configured to input the first feature representations into a second feature extracting neural network to generate respective second feature representations, each associated with one of the ultrasound images and wherein the one or more extracted feature representations include the second feature representations.

27. The system of claim 22 wherein the at least one processor is configured to input the one or more extracted feature representations into a quality assessment value specific neural network and to input the one or more extracted feature representations into an image property specific neural network.

28. The system of claim 27 wherein the at least one processor is configured to input each of the one or more extracted feature representations into an implementation of a commonly defined quality assessment value specific neural subnetwork and to input each of the one or more extracted feature representations into an implementation of a commonly defined image property specific neural network.

29. The system of claim 22 wherein the at least one processor is configured to produce signals for causing a representation of the quality assessment value and a representation of the image property to be displayed by at least one display in association with the set of ultrasound images.

30. A system for facilitating ultrasonic image analysis, the system comprising:
means for receiving signals representing a set of ultrasound images of the subject;
means for deriving one or more extracted feature representations from the set of ultrasound images;
means for determining, based on the derived one or more extracted feature representations, a quality assessment value representing a quality assessment of the set of ultrasound images;
means for determining, based on the derived one or more extracted feature representations, an image property associated with the set of ultrasound images; and
means for producing signals representing the quality assessment value and the image property for causing the quality assessment value and the image property to be associated with the set of ultrasound images.

* * * * *